(12) United States Patent
Kang et al.

(10) Patent No.: US 10,765,647 B2
(45) Date of Patent: Sep. 8, 2020

(54) COMPOSITION FOR TREATING DIABETES, CONTAINING EXTRACT OF YUKMIJIHWANGTANG

(71) Applicant: COMPREHENSIVE AND INTEGRATIVE MEDICINE INSTITUTE, Daegu (KR)

(72) Inventors: Seok Bong Kang, Gyeongsangbuk-do (KR); Ho Sang Sohn, Daegu (KR); Joon Seok Byun, Daegu (KR); Ki Cheul Sohn, Daegu (KR); Sae Kwang Ku, Daegu (KR)

(73) Assignee: COMPREHENSIVE AND INTEGRATIVE MEDICINE INSTITUTE, Daegu (KR)

(*) Notice: Subject to any disclaimer, the term of this patent is extended or adjusted under 35 U.S.C. 154(b) by 0 days.

(21) Appl. No.: 15/970,282

(22) Filed: May 3, 2018

(65) Prior Publication Data

US 2019/0046477 A1 Feb. 14, 2019

Related U.S. Application Data

(63) Continuation of application No. 14/889,076, filed as application No. PCT/KR2014/003978 on May 2, 2014, now abandoned.

(30) Foreign Application Priority Data

May 7, 2013 (KR) .................. 10-2013-0051473

(51) Int. Cl.

| A61K 31/155 | (2006.01) |
|---|---|
| A61K 36/884 | (2006.01) |
| A61K 36/8945 | (2006.01) |
| A61K 36/40 | (2006.01) |
| A61K 36/65 | (2006.01) |
| A61K 36/804 | (2006.01) |
| A61K 36/076 | (2006.01) |
| A61K 36/53 | (2006.01) |

(52) U.S. Cl.
CPC .......... *A61K 31/155* (2013.01); *A61K 36/076* (2013.01); *A61K 36/40* (2013.01); *A61K 36/53* (2013.01); *A61K 36/65* (2013.01); *A61K 36/804* (2013.01); *A61K 36/884* (2013.01); *A61K 36/8945* (2013.01)

(58) Field of Classification Search
None
See application file for complete search history.

(56) References Cited

U.S. PATENT DOCUMENTS

| 6,376,549 B1 | 4/2002 | Fine et al. |
| 6,498,193 B2 | 12/2002 | Beisswenger et al. |

FOREIGN PATENT DOCUMENTS

| KR | 10-1998-0033798 A | 8/1998 |
| KR | 10-1990-0017602 A | 12/1999 |
| KR | 10-2002-0094179 A | 12/2002 |
| KR | 10-2011-0021691 A | 3/2011 |

OTHER PUBLICATIONS

English translation of Pyo (KR 2002094179 A) 2002.*
Ha et al., "Safety Evaluation of Yukmijihwang-tang: Assessment of Acute and Subchronic Toxicity in Rats", Evidence-Based Complementary and Alternative Medicine, 2010, vol. 2011, Article ID 672136, pp. 1-8.
Poon et al., "Review of the effects of the traditional Chinese medicine Rehmannia Six Formula on diabetes mellitus and its complications", Journal of Diabetes, 2011, vol. 3, pp. 164-200.
Wu et al., "Increase of insulin sensitivity in diabetic rats received Die-Huang-Wan, a herbal mixture used in Chinese traditional medicine", Acta Pharmacol Sin, 2002, vol. 23, No. 12, pp. 1181-1187.
International Search Report and Written Opinion for International Application No. PCT/KR2014/003978 (6 Pages) (dated Sep. 25, 2014).

* cited by examiner

*Primary Examiner* — Susan Hoffman
(74) *Attorney, Agent, or Firm* — Lucas & Mercanti, LLP

(57) ABSTRACT

Provided is a composition for treating diabetes, including a hypoglycemic agent and a Yukmijihwang-tang extract. More particularly, the hypoglycemic agent is administered into an individual, and the Yukmijihwang-tang extract is administered into the individual, thereby considerably increasing a hypoglycemic effect of the hypoglycemic agent, and preventing and reducing various diabetic complications such as diabetes and diabetic liver damage, renal damage, hyperlipidemia immunosuppression and ocular damage.

11 Claims, 20 Drawing Sheets

Fig.1

| Herbs | Scientific Names | Amounts (g) |
|---|---|---|
| Rehmanniae Radix Preparat | *Rehmannia glutinosa* Liboschitz var. *urpurea* Makino | 2 |
| Dioscoreae Rhizoma | *Dioscorea batatas* Decaisne | 1 |
| Corni Fructus | *Cornus Officinalis* Siebold et Zuccarini | 1 |
| Hoelen | *Poria cocos* Wolf | 1 |
| Moutan Cortex | *Paeonia suffruticosa* Andrews | 1 |
| Alismatis Rhizoma | *Alisma orientale* Juzepczuk | 1 |
| Total | 6 types | 7 |

YMJHT = *Yukmijihwang-tang*, purchase from Korea INS Pharm. (Hwasoon, Korea)

Fig.2

| Parameters | Metformin (500mg/kg) | |
|---|---|---|
| | Without YMJHT co-administration (Distill water) | With YMJHT co-administration (100mg/kg) |
| Cmax (μg/ml) | 1.10±0.55 | 0.90±0.22 |
| Tmax (hrs) | 25.82±3.06 | 23.24±3.83 |
| $AUC_{0-t}$ (hr·μg/ml) | 147.63±24.37 | 156.57±27.06 |
| $AUC_{0-inf}$ (hr·μg/ml) | 177.06±35.17 | 200.00±29.04 |
| $t_{1/2}$ (hr) | 9.23±3.23 | 10.56±1.73 |
| $MRT_{inf}$ (hr) | 11.35±5.18 | 14.44±2.65 |

Values are expressed as mean ± SD of five rats

YMJHT = *Yukmijihwang-tang*, purchase from Korea INS Pharm. (Hwasoon, Korea)
Cmax: The peak plasma concentration
Tmax: Time to reach Cmax
$AUC_{0-t}$: The total area under the plasma concentration-time curve from time zero to time measured
$AUC_{0-inf}$: The total area under the plasma concentration-time curve from time zero to time infinity
$t_{1/2}$: half life
$MRT_{inf}$: mean residence to time infinity

Fig. 5A

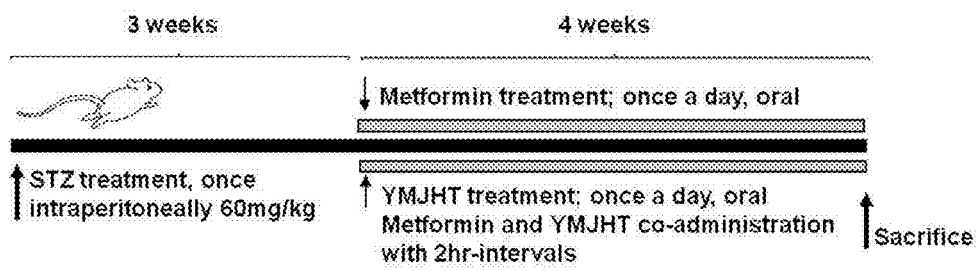

Fig. 5B

| Group | Pretreatment | Dose (mg/kg/day) | Animal No. |
|---|---|---|---|
| DMe007-PD: Effects on STZ-induced type I diabetic rats | | | |
| Control | Saline | Vehicle 5ml/kg | R01~R08 |
| Control | STZ | Vehicle 5ml/kg | R09~R16 |
| Reference | STZ | Metformin single (500mg/kg) | R17~R24 |
| Reference | STZ | YMJHT single (400mg/kg) | R25~R32 |
| Active | STZ | Metformin and YMJHT (500 and 100mg/kg) | R33~R40 |
| Active | STZ | Metformin and YMJHT (500 and 200mg/kg) | R41~R48 |
| Active | STZ | Metformin and YMJHT (500 and 400mg/kg) | R49~R56 |

Fig. 7A

| Groups | Blood glucose levels (mg/dl) | | |
|---|---|---|---|
| | At 21 days after STZ treatment | At a terminations | Changes after 28 days of test article treatments |
| Controls | | | |
| Vehicle | 94.25±6.36 | 104.25±9.05 | 10.00±9.50 |
| STZ | 297.88±33.03$^a$ | 566.00±91.79$^g$ | 268.13±95.54$^g$ |
| Single treated | | | |
| Metformin | 302.88±28.52$^a$ | 411.75±43.53$^{gh}$ | 108.88±52.09$^{gh}$ |
| YMJHT | 296.88±29.05$^a$ | 459.38±44.60$^{gik}$ | 162.50±56.30$^{gk}$ |
| Metformin and YMJHT co-administered with 2hr-intervals | | | |
| 100mg/kg | 294.00±26.52$^a$ | 400.00±61.37$^{gh}$ | 106.00±50.55$^{gh}$ |
| 200mg/kg | 297.75±31.09$^a$ | 342.25±30.63$^{ghj}$ | 44.50±23.87$^{ghk}$ |
| 400mg/kg | 298.13±28.53$^a$ | 298.50±20.02$^{ghj}$ | 0.38±22.14$^{hj}$ |

Fig. 7B

| Groups | Pancreas weights | |
|---|---|---|
| | Absolute (g) | Relative (%) |
| Controls | | |
| Vehicle | 0.580±0.109 | 0.226±0.034 |
| STZ | 0.522±0.075 | 0.405±0.054$^a$ |
| Single treated | | |
| Metformin | 0.564±0.058 | 0.374±0.042$^a$ |
| YMJHT | 0.509±0.036$^b$ | 0.351±0.036$^{ad}$ |
| Metformin and YMJHT co-administered with 2hr-intervals | | |
| 100mg/kg | 0.560±0.078 | 0.371±0.066$^a$ |
| 200mg/kg | 0.572±0.044 | 0.331±0.050$^{ac}$ |
| 400mg/kg | 0.585±0.052 | 0.345±0.046$^{ad}$ |

Fig. 7C

| Groups | Histomorphometry | | Immunoreactive cells | |
|---|---|---|---|---|
| | Number of pancreatic islets (/100mm$^2$) | Mean diameters of pancreatic islets (μm) | Number of insulin cells (/mm$^2$ of islet) | Number of glucagon cells (/mm$^2$ of islet) |
| Controls | | | | |
| Vehicle | 22.00±3.02 | 176.45±29.34 | 624.13±98.97 | 121.00±24.02 |
| STZ | 5.38±1.60$^a$ | 45.02±11.15$^a$ | 33.50±9.75$^g$ | 635.88±80.51$^a$ |
| Single treated | | | | |
| Metformin | 11.88±2.42$^{ac}$ | 89.04±19.05$^{ac}$ | 101.50±30.50$^{gh}$ | 459.25±122.07$^{ac}$ |
| YMJHT | 10.38±1.60$^{ac}$ | 86.76±17.54$^{ac}$ | 86.63±18.64$^{gh}$ | 474.25±111.63$^{ac}$ |
| Metformin and YMJHT co-administered with 2hr-intervals | | | | |
| 100mg/kg | 10.75±2.49$^{ac}$ | 90.73±21.56$^{ac}$ | 92.13±11.67$^{gh}$ | 458.13±123.41$^{ac}$ |
| 200mg/kg | 14.63±2.26$^{acf}$ | 120.95±23.74$^{ace}$ | 140.88±27.47$^{ghk}$ | 323.00±90.99$^{ace}$ |
| 400mg/kg | 19.00±1.85$^{acf}$ | 140.57±22.76$^{ace}$ | 184.63±30.00$^{ghj}$ | 259.38±76.51$^{ace}$ |

Fig. 9A

| Groups | Serum levels (IU/L) | |
|---|---|---|
| | Aspartate aminotransferase; ALT | Alanine aminotransferase; AST |
| Controls | | |
| Vehicle | 101.25±23.60 | 40.13±10.66 |
| STZ | 1098.25±182.47$^f$ | 451.13±101.75$^f$ |
| Single treated | | |
| Metformin | 737.75±161.87$^{fh}$ | 303.50±27.71$^{fh}$ |
| YMJHT | 558.88±118.41$^{fhj}$ | 233.13±29.35$^{fhi}$ |
| Metformin and YMJHT co-administered with 2hr-intervals | | |
| 100mg/kg | 664.75±148.25$^{fh}$ | 281.63±73.90$^{fh}$ |
| 200mg/kg | 485.13±80.48$^{fhj}$ | 186.25±25.64$^{fhi}$ |
| 400mg/kg | 307.00±82.46$^{fhi}$ | 128.63±44.61$^{fhi}$ |

Fig. 9B

| Groups | Liver weights | | Histomorphometry | |
|---|---|---|---|---|
| | Absolute (g) | Relative (%) | Degenerative cell regions (%) | Number of hepatocyte (/mm$^2$) |
| Controls | | | | |
| Vehicle | 6.074±0.450 | 2.383±0.145 | 5.50±4.11 | 576.50±113.77 |
| STZ | 8.470±0.687$^a$ | 6.639±1.179$^f$ | 74.53±10.89$^a$ | 196.63±33.50$^f$ |
| Single treated | | | | |
| Metformin | 7.252±0.801$^{ac}$ | 4.801±0.380$^{fh}$ | 52.46±9.84$^{ac}$ | 315.75±55.53$^{fh}$ |
| YMJHT | 7.361±0.426$^{ac}$ | 5.074±0.494$^{fh}$ | 45.00±6.91$^{ac}$ | 339.63±43.56$^{fh}$ |
| Metformin and YMJHT co-administered with 2hr-intervals | | | | |
| 100mg/kg | 7.340±0.727$^{ac}$ | 4.854±0.496$^{fh}$ | 43.92±10.84$^{ace}$ | 352.63±68.36$^{fh}$ |
| 200mg/kg | 7.227±0.467$^{ac}$ | 4.177±0.523$^{fhj}$ | 31.80±7.36$^{acd}$ | 400.38±63.84$^{ghd}$ |

Values are expressed mean ± S.D. of eight rats

Fig. 11A

| Groups | Serum levels (IU/L) | |
|---|---|---|
| | Blood nitrogen urea; BUN | Creatinine |
| Controls | | |
|   Vehicle | 19.50±3.46 | 0.66±0.12 |
|   STZ | 96.63±12.59$^a$ | 1.84±0.24$^a$ |
| Single treated | | |
|   Metformin | 66.00±10.20$^{ab}$ | 1.26±0.19$^{ab}$ |
|   YMJHT | 63.00±10.93$^{ab}$ | 1.19±0.22$^{ab}$ |
| Metformin and YMJHT co-administered with 2hr-intervals | | |
|   100mg/kg | 63.50±10.32$^{ab}$ | 1.11±0.21$^{ab}$ |
|   200mg/kg | 43.63±11.16$^{abc}$ | 0.99±0.16$^{abc}$ |
|   400mg/kg | 27.13±6.38$^{bc}$ | 0.81±0.08$^{bc}$ |

Fig. 11B

| Groups | Kidney weights | | Histomorphometry | |
|---|---|---|---|---|
| | Absolute (g) | Relative (%) | Vasodilated atrophic glomeruli (/100 glomerulus) | Vacuolated and atrophic tubules (/100 tubules) |
| Controls | | | | |
|   Vehicle | 0.736±0.074 | 0.288±0.013 | 2.00±1.85 | 6.38±4.27 |
|   STZ | 1.238±0.152$^a$ | 0.961±0.115$^a$ | 75.13±10.66$^e$ | 77.75±10.99$^e$ |
| Single treated | | | | |
|   Metformin | 0.974±0.064$^{ab}$ | 0.650±0.082$^{ab}$ | 47.38±10.03$^{ef}$ | 54.50±12.02$^{ef}$ |
|   YMJHT | 1.045±0.091$^{ab}$ | 0.720±0.086$^{ab}$ | 50.25±11.65$^{ef}$ | 52.00±13.61$^{ef}$ |
| Metformin and YMJHT co-administered with 2hr-intervals | | | | |
|   100mg/kg | 0.999±0.080$^{ab}$ | 0.664±0.093$^{ab}$ | 47.25±10.10$^{ef}$ | 54.88±13.11$^{ef}$ |
|   200mg/kg | 0.957±0.074$^{ab}$ | 0.552±0.067$^{abd}$ | 23.50±8.77$^{efg}$ | 27.25±8.28$^{efg}$ |
|   400mg/kg | 0.858±0.072$^{abd}$ | 0.505±0.053$^{abc}$ | 11.38±2.33$^{efg}$ | 18.00±2.51$^{efg}$ |

Values are expressed mean ± S.D. of eight rats

Fig. 13

| Groups | Serum levels (mg/dl) | | | |
|---|---|---|---|---|
| | Total cholesterol | Triglyceride | Low density lipoprotein; LDL | High density lipoprotein; HDL |
| Controls | | | | |
| Vehicle | 68.25±13.23 | 28.50±12.43 | 5.75±1.67 | 61.38±12.63 |
| STZ | 218.38±25.77[a] | 594.63±105.82[d] | 17.63±2.62[a] | 22.13±4.42[d] |
| Single treated | | | | |
| Metformin | 151.63±19.12[ab] | 417.88±110.44[ae] | 12.50±1.41[ab] | 28.13±3.40[a,f] |
| YMJHT | 153.25±16.60[ab] | 363.88±64.74[ae] | 12.38±1.51[ab] | 30.63±6.02[a,f] |
| Metformin and YMJHT co-administered with 2hr-intervals | | | | |
| 100mg/kg | 143.50±12.38[ab] | 370.75±94.01[ae] | 12.50±2.51[ab] | 29.13±2.80[a,e] |
| 200mg/kg | 126.75±17.13[abc] | 245.63±58.51[deg] | 10.63±1.69[ae] | 35.75±5.42[a,d,h] |
| 400mg/kg | 102.00±20.30[abc] | 155.13±48.84[deg] | 9.50±2.20[abc] | 38.38±7.89[a,d,h] |

Values are expressed mean ± S.D. of eight rats

Fig. 14A

| Groups | Thymus weights | | Spleen weights | |
| --- | --- | --- | --- | --- |
| | Absolute (g) | Relative (%) | Absolute (g) | Relative (%) |
| Controls | | | | |
|   Vehicle | 0.464±0.055 | 0.182±0.018 | 0.488±0.071 | 0.191±0.016 |
|   STZ | 0.060±0.023[g] | 0.046±0.017[a] | 0.170±0.035[a] | 0.131±0.025[a] |
| Single treated | | | | |
|   Metformin | 0.104±0.026[gi] | 0.069±0.017[ad] | 0.223±0.024[ad] | 0.147±0.008[a] |
|   YMJHT | 0.104±0.026[gi] | 0.071±0.017[ad] | 0.237±0.032[ac] | 0.163±0.020[bd] |
| Metformin and YMJHT co-administered with 2hr-intervals | | | | |
|   100mg/kg | 0.118±0.029[gi] | 0.079±0.023[ad] | 0.230±0.040[ac] | 0.153±0.032[a] |
|   200mg/kg | 0.183±0.036[gij] | 0.105±0.017[ade] | 0.301±0.037[ace] | 0.174±0.028[cf] |
|   400mg/kg | 0.237±0.023[gij] | 0.139±0.016[ade] | 0.312±0.046[ace] | 0.184±0.031[ce] |

Fig. 14B

| Groups | Histomorphometry: thymus | |
| --- | --- | --- |
| | Lobular total thickness (μm/lobes) | Lobular cortex thickness (μm/lobes) |
| Controls | | |
|   Vehicle | 2450.14±357.50 | 1394.92±265.47 |
|   STZ | 638.93±170.24[a] | 191.39±29.17[g] |
| Single treated | | |
|   Metformin | 1137.29±153.89[ac] | 572.04±159.06[gi] |
|   YMJHT | 1129.55±255.91[ac] | 597.11±206.81[gi] |
| Metformin and YMJHT co-administered with 2hr-intervals | | |
|   100mg/kg | 1222.01±270.17[ac] | 590.55±99.45[gi] |
|   200mg/kg | 1668.34±253.51[ace] | 842.32±216.09[gik] |
|   400mg/kg | 1921.66±148.98[ace] | 1088.33±157.99[hij] |

Fig. 14C

| Groups | Histomorphometry: spleen | | |
| --- | --- | --- | --- |
| | Total thickness (mm/ central region of spleen) | Numbers of white pulps (/100mm² of spleen) | Mean diameters of white pulps (μm) |
| Controls | | | |
|   Vehicle | 2801.93±376.88 | 42.50±10.69 | 605.60±141.02 |
|   STZ | 1443.11±328.28[g] | 12.25±2.66[g] | 160.81±39.83[g] |
| Single treated | | | |
|   Metformin | 1968.90±116.60[gi] | 21.63±2.62[gi] | 341.63±52.48[gi] |
|   YMJHT | 2010.12±200.32[gi] | 21.75±3.65[gi] | 351.33±47.05[gi] |
| Metformin and YMJHT co-administered with 2hr-intervals | | | |
|   100mg/kg | 1972.37±189.66[gi] | 21.88±2.53[gi] | 342.59±53.29[gi] |
|   200mg/kg | 2280.22±277.97[hij] | 28.50±3.07[gij] | 474.96±75.13[hij] |
|   400mg/kg | 2415.72±357.51[hij] | 31.75±4.13[hij] | 575.43±80.97[ij] |

Fig. 17A

```
Score 0: clear
Score 1: peripheral vesicles and opacities
Score 2: central opacities
Score 3: diffused opacities
Score 4: mature cataract
Score 5: hypermature cataract
Max = 5
```
[Ao et al., 1991; Suryanarayana et al., 2003; Kametaka et al., 2008]

Representative Images of Cataract Scores

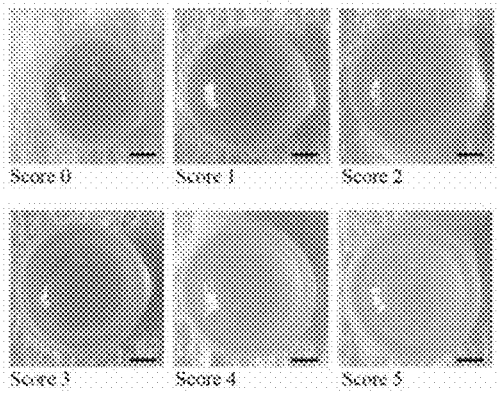

Scoring was based on the opaque of lens in the present study
Scale bars = 1mm

Fig. 17B

```
Normal: score 0
Mild: score 1
Moderate: score 2
Severe: score 3
Max = 3
```
[Yoshida et al., 2004]

Representative Images of Eyeball Histopathological Damage Scores

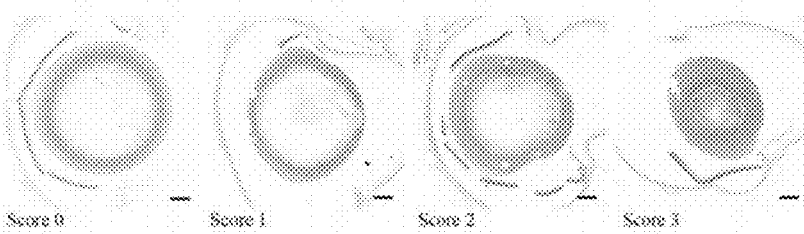

Scoring was based on the thicknesses and severities of eosinophilic disarranged lenticular fiber regions in the present study
Scale bars = 400μm

Fig. 18A

| Groups | Cataract Scores | |
|---|---|---|
| | Observer-based scores [Fig 3] | Quantitative image-analysis scores (%) |
| Controls | | |
| Vehicle | 0.50±0.53 | 8.42±3.19 |
| STZ | 4.50±0.53$^a$ | 55.04±7.36$^a$ |
| Single treated | | |
| Metformin | 2.75±0.71$^{ac}$ | 32.71±7.23$^{ac}$ |
| YMJHT | 3.13±0.64$^{ac}$ | 35.99±5.75$^{ac}$ |
| Metformin and YMJHT co-administered with 2hr-intervals | | |
| 100mg/kg | 3.00±0.76$^{ac}$ | 34.34±5.87$^{ac}$ |
| 200mg/kg | 1.88±0.64$^{ace}$ | 24.70±4.82$^{ace}$ |
| 400mg/kg | 1.50±0.76$^{acd}$ | 19.68±7.71$^{acd}$ |

Fig. 18B

| Groups | Histomorphometry: Lens | |
|---|---|---|
| | Eyeball damage score [Fig 4] | Thickness of eosinophilic disarranged lenticular fiber regions (μm/lens) |
| Controls | | |
| Vehicle | 0.25±0.46 | 404.65±115.74 |
| STZ | 2.63±0.52$^a$ | 1431.08±244.79$^a$ |
| Single treated | | |
| Metformin | 1.75±0.71$^{ac}$ | 767.96±141.59$^{ac}$ |
| YMJHT | 1.63±0.74$^{ac}$ | 787.82±195.82$^{ac}$ |
| Metformin and YMJHT co-administered with 2hr-intervals | | |
| 100mg/kg | 1.38±0.52$^{ac}$ | 691.31±168.15$^{ac}$ |
| 200mg/kg | 1.00±0.53$^{bce}$ | 510.36±121.10$^{cd}$ |
| 400mg/kg | 0.75±0.71$^{cd}$ | 406.10±84.58$^{cd}$ |

Fig. 18C

| Groups | Histomorphometry: Retina | | | |
|---|---|---|---|---|
| | Total thicknesses (μm/retina) | Inner plexiform layer thickness (μm/retina) | Inner nuclear layer thickness (μm/retina) | Number of blood vessels in retina (/mm of retina) |
| Controls | | | | |
| Vehicle | 226.11±35.27 | 72.68±8.57 | 45.19±6.50 | 1.50±0.93 |
| STZ | 103.63±10.31$^a$ | 31.93±6.13$^a$ | 19.13±1.69$^f$ | 12.63±2.67$^a$ |
| Single treated | | | | |
| Metformin | 138.30±15.50$^{ac}$ | 42.16±5.26$^{ac}$ | 27.60±3.21$^{fh}$ | 7.00±1.31$^{ac}$ |
| YMJHT | 135.44±12.68$^{ac}$ | 42.11±7.67$^{ac}$ | 29.47±2.46$^{fh}$ | 7.38±1.30$^{ac}$ |
| Metformin and YMJHT co-administered with 2hr-intervals | | | | |
| 100mg/kg | 138.74±18.59$^{ac}$ | 42.94±3.85$^{ac}$ | 28.54±3.48$^{fh}$ | 7.13±1.36$^{ac}$ |
| 200mg/kg | 161.80±16.50$^{ace}$ | 53.46±8.02$^{acd}$ | 33.89±5.09$^{ghj}$ | 5.13±1.55$^{ace}$ |
| 400mg/kg | 180.48±24.96$^{acd}$ | 66.09±7.40$^{cd}$ | 39.05±4.13$^{hi}$ | 3.75±1.75$^{acd}$ |

Fig. 20

| Groups | Lipid peroxidation Malondialdehyde (nM/g protein) | Endogenous Antioxidant Glutathione (µM/g protein) | Endogenous Antioxidative Enzymes (U/mg protein) | |
|---|---|---|---|---|
| | | | Superoxide dismutase; SOD | Catalase |
| Controls | | | | |
| Vehicle | 89.88±14.73 | 147.63±29.94 | 212.13±25.65 | 444.88±102.25 |
| STZ | 225.75±30.07[b] | 39.25±14.04[f] | 93.50±18.74[f] | 176.75±46.67[f] |
| Single treated | | | | |
| Metformin | 152.25±16.30[ac] | 64.63±11.94[a] | 141.63±16.27[ac] | 262.63±31.34[a] |
| YMJHT | 151.50±13.12[ac] | 67.00±11.83[a] | 145.00±17.51[ac] | 260.50±46.39[a] |
| Metformin and YMJHT co-administered with 2hr-intervals | | | | |
| 100mg/kg | 144.13±20.54[ac] | 66.00±10.00[a] | 148.63±13.11[ac] | 263.38±34.13[a] |
| 200mg/kg | 127.38±18.20[ace] | 79.13±9.49[ab] | 174.75±14.95[acd] | 302.88±20.15[a] |
| 400mg/kg | 109.75±11.57[acd] | 88.63±16.57[ad] | 185.00±10.17[acd] | 339.00±55.06[da] |

Values are expressed mean ± S.D. of eight rats

COMPOSITION FOR TREATING DIABETES, CONTAINING EXTRACT OF YUKMIJIHWANGTANG

CROSS-REFERENCE TO RELATED APPLICATIONS

This application is a continuation of U.S. patent application Ser. No. 14/889,076 filed Nov. 4, 2015, now abandoned, which is a 371 of PCT/KR2014/003978, filed May 2, 2014, which claims the benefit of Korean Patent Application No. 10-2013-0051473, filed May 7, 2013, the contents of each of which are incorporated herein by reference.

BACKGROUND

Field of the Invention

The present invention relates to a composition for treating diabetes, which includes a hypoglycemic agent and a Yukmijihwang-tang extract.

Discussion of Related Art

Diabetes refers to a group of metabolic diseases which are caused by insufficient secretion of insulin or malfunctioning of insulin, characterized by hyperglycemia in which the concentration of glucose in blood is increased, and have several symptoms and signs due to hyperglycemia such as excretion of glucose by urine. The diabetes and their complications are serious diseases having a high death rate globally as well as cancer, renal and circulatory diseases, and according to the report of the American Diabetes Society, even today, the diabetic death rate is continuously increasing.

Compared with healthy people, patients with diabetes is highly likely to have complications such as eye diseases, renal diseases, heart diseases, etc. In the case of mild hyperglycemia, since most patients do not or vaguely recognize symptoms, it is difficult to think that they have diabetes. For this reason, the hyperglycemic state is maintained for a long time, and in most cases, several complications are found when they start to occur in the body. Diagnosis is generally performed through a blood test. When a blood sugar level 8 hours after fasting is detected at 126 mg/dL or more, a blood sugar level is detected at 200 mg/dL or more 2 hours after an oral glucose tolerance test, or even when a blood sugar level detected regardless of a meal is 200 mg/dL or more, such conditions can be diagnosed as diabetes.

Today, acute or fatal symptoms of diabetes are being reduced due to insulin therapy, but insulin does not have a noticeable effect on the symptoms occurring over a long period. Diabetes is classified into insulin-dependent diabetes and non-insulin-dependent diabetes. The insulin-dependent diabetes is referred to as type I diabetes, and the non-insulin-dependent diabetes is referred to as type II diabetes. The insulin-dependent diabetes has a characteristic of severely destroying pancreatic beta cells secreting insulin, thereby reducing insulin and increasing blood sugar.

The type I diabetes needs insulin therapy, and the type II diabetes needs a change of lifestyle habits and drug administration. Edible hypoglycemic agents are mainly divided into an insulin secretagogue and an insulin sensitivity enhancer. Among these, the insulin sensitivity enhancer is characterized by almost no hypoglycemia when administered, and a biguanide-based drug, metformin, is generally used. However, when metformin is administered alone, side effects such as diabetic liver damage, renal damage, hyperlipidemia, immunosuppression, and ocular damage occur, and therefore, there is an increasing demand for a method of administering metformin having an excellent drug efficacy without side effects.

Meanwhile, Yukmijihwang-tang is a representative formulation frequently used in Oriental medicine for various renal diseases, and is a composite formulation composed of a total of six natural substances including *Rehmanniae Radix Preparat, Dioscoreae Rhizoma, Corni Fructus, Alismatis Rhizoma, Hoelen*, and *Moutan Cortex*.

SUMMARY OF THE INVENTION

The present invention is directed to providing a composition for treating diabetes using a Yukmijihwang-tang extract.

However, technical objects to be accomplished in the present invention are not limited to the above-described object, and other objects which will not be described will be clearly understood to those of ordinary skill in the art from the following descriptions.

One aspect of the present invention provides a composition for treating diabetes, which includes a hypoglycemic agent and a Yukmijihwang-tang extract.

In one embodiment of the present invention, the hypoglycemic agent is metformin.

In another embodiment of the present invention, the Yukmijihwang-tang extract may include *Rehmanniae Radix Preparat, Dioscoreae Rhizoma, Corni Fructus, Alismatis Rhizoma, Hoelen*, and *Moutan Cortex*.

In still another embodiment of the present invention, the hypoglycemic agent and the Yukmijihwang-tang extract may be premixed to be formulated, or separately formulated.

In yet another embodiment of the present invention, the hypoglycemic agent and the Yukmijihwang-tang extract may be parenterally, orally, locoregionally, or percutaneously administered.

In yet another embodiment of the present invention, the administration of the Yukmijihwang-tang extract may start 30 minutes to 4 hours after the administration of the hypoglycemic agent.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 1 is a table showing the composition of Yukmijihwang-tang;

FIG. 2 shows comparison of $C_{max}$, $T_{max}$, AUC, $t_{1/2}$, and $MRT_{inf}$ values for a metformin single treated group and a group to which Yukmijihwang-tang is administered within 5 minutes after metformin treatment;

FIG. 5A is a schematic diagram illustrating an experiment method and FIG. 5B is a design of experimental groups according to Example 3;

FIG. 7A shows an antidiabetic evaluation, FIG. 7B shows pancreas weight change, and FIG. 7C shows histopahological and immunological changes in pancreas through Yukmijihwang-tang co-administration;

FIG. 9A shows changes in AST and ALT variations, and FIG. 9B shows liver weights and histopathological changes through the Yukmijihwang-tang co-administration;

FIG. 11A shows changes in blood creatinine and BUN contents, and FIG. 11B shows kidney weights change and numerical changes in degenerated glomeruli and renal tubules to identify a kidney protecting effect;

FIG. 13 shows changes in total cholesterol, LDL and HDL levels in blood to identify an antihyperlipidemic effect;

FIG. 14A shows changes in thymus and spleen weight, FIG. 14B shows changes in total thicknesses of thymus cortex and lobules, and FIG. 14C shows changes in spleen thickness, and the number and mean diameter of white pulps to identify an immune activity effect;

FIG. 17A shows cataract scoring criteria for observer-based scores and FIG. 17B shows cataract scoring criteria for quantitative image scores;

FIG. 18A shows observer-based scores and quantitative image scores for cataract by group, FIG. 18B shows histomorphological changes in lens by group and FIG. 18C shows histomorphological changes in retina by group;

FIG. 20 shows changes in a lipid peroxidation indicator, MDA in renal tissues, changes in GSH content, and catalase and SOD activities to identify an antioxidative defense effect of the kidney.

DETAILED DESCRIPTION OF EXEMPLARY EMBODIMENTS

Figure 3:
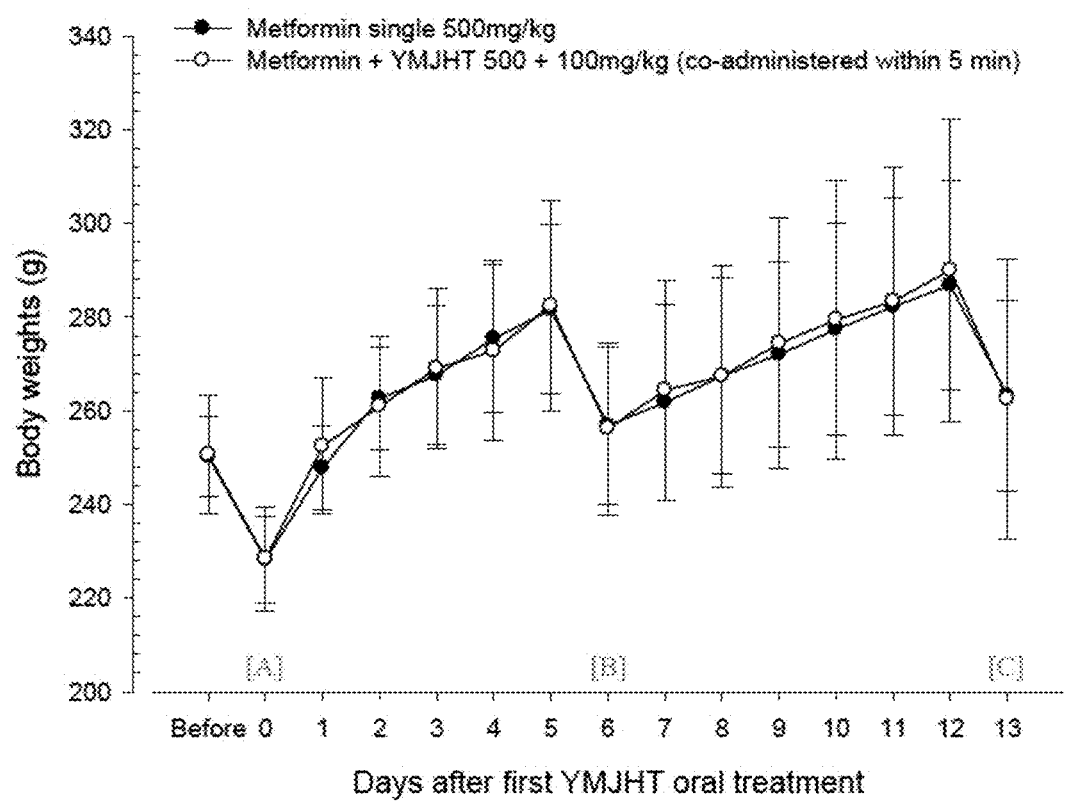
FIG. 3 shows changes in body weights for the metformin single treated group and a group in which only Yukmijihwang-tang is repeatedly oral-administered for 6 days, and then the Yukmijihwang-tang is co-administered within 5 minutes after repeated administration of metformin for 8 days.

Exemplary embodiments of the present invention will be described in detail below with reference to the accompanying drawings. While the present invention is shown and described in connection with exemplary embodiments thereof, it will be apparent to those skilled in the art that various modifications can be made without departing from the spirit and scope of the invention.

The present inventors focused on an oriental medicine to develop a composition which could reduce various side effects occurring when a hypoglycemic agent was administered to treat diabetes, and further increase a hypoglycemic effect, and confirmed that Yukmijihwang-tang among such oriental medicines has excellent effects on reducing a blood sugar level and reducing side effects, thereby completing the present invention.

Accordingly, the present invention is directed to providing a composition for treating diabetes, which includes a hypoglycemic agent and a Yukmijihwang-tang extract.

The term "Yukmijihwang-tang extract" used herein refers to an extract that is extracted from six medicinal herbs. The six medicinal herbs include *Rehmanniae Radix Preparat*, *Dioscoreae Rhizoma*, *Corni Fructus*, *Alismatis Rhizoma*, *Hoelen*, and *Moutan Cortex*.

In one exemplary embodiment of the present invention, the hypoglycemic agent and the Yukmijihwang-tang extract may be premixed and formulated, or separately formulated.

The Yukmijihwang-tang extract may be administered within 30 minutes to 4 hours after the administration of the hypoglycemic agent, preferably 1 to 3 hours, and most preferably 1.5 to 2.5 hours, and also administered 2 hours after the administration of the hypoglycemic agent as described in the exemplary embodiment of the present invention, but the present invention is not limited thereto.

The hypoglycemic agent used herein is metformin, but the present invention is not limited thereto.

The hypoglycemic agent and the Yukmijihwang-tang extract may be administered parenterally, orally, locoregionally, or percutaneously. The Yukmijihwang-tang extract is preferably administrated orally, but the administration route may be suitably selected by those skilled in the art depending on a patient's condition and body weight, severity of a disease, and a duration of administration.

The term "individuals" used herein refers to subjects having a disease to be treated, and more specifically, mammals such as humans or non-human primates, mice, rats, dogs, cats, horses, cattle, etc.

Also, the present invention may provide a composition for treating diabetes, which includes a Yukmijihwang-tang extract.

The pharmaceutical composition of the present invention may include a pharmaceutically acceptable carrier.

The pharmaceutically acceptable carrier may include a normal saline solution, polyethylene glycol, ethanol, vegetable oils, isopropyl myristate and the like, but the present invention is not limited thereto.

In an exemplary embodiment of the present invention, a preferred dose of the pharmaceutical composition may vary depending on a patient's condition and body weight, severity of a disease, a dosage form, and administration route and duration, but may be suitably selected by those skilled in the related art. However, the composition is preferably administered daily at a dose of 0.001 to 300 mg/kg (body weight), and more preferably, 0.01 to 200 mg/kg (body weight).

The pharmaceutical composition according to the present invention may be administered to a mammal such as a rat, a mouse, livestock, and a human through various routes of administration. Methods of administration are not particularly limited. For example, the composition may be administered orally, or rectally, or by intravenous, intramuscular, subcutaneous, cervical epidural, or intracerebroventricular injection.

The composition for treating diabetes according to the present invention, which includes the Yukmijihwang-tang extract, may enhance a hypoglycemic effect, and simultaneously reduce several side effects occurring when the hypoglycemic agent is conventionally administered alone.

Hereinafter, exemplary embodiments according to the present invention will be provided to help in understanding of the present invention. However, the following examples are merely provided such that the present invention can be more easily understood, and the scope of the present invention is not limited to the following examples.

EXAMPLES

In examples, the influence of Yukmijihwang-tang co-administration pharmacokinetics, for example, absorption and excretion, of a hypoglycemic agent was identified, and a synergistic effect of the co-administration of Yukmijihwang-tang on a drug efficacy of the hypoglycemic agent was evaluated by selecting a co-administration method that did not influence the pharmacokinetics. To evaluate the influence on the pharmacokinetics of the hypoglycemic agent through the co-administration of Yukmijihwang-tang, co-administration of the Yukmijihwang-tang orally once within 5 minutes after the administration of the hypoglycemic agent (Example 1), orally repeated pre-administration of the Yukmijihwang-tang for 6 days and orally repeated co-administration of the Yukmijihwang-tang for 8 days within 5 minutes (Example 2), and co-administration at 2-hour intervals (Example 3) were performed. The influence of the co-administration of the Yukmijihwang-tang on the drug efficacy of the hypoglycemic agent was identified using rats with type I diabetes induced by streptozotocin administration.

The hypoglycemic agent used herein was metformin (Wako, Osaka, Japan), and the Yukmijihwang-tang (hereinafter, referred to as "YMJHT") was purchased from Inspharm, Korea, and the composition is as shown in FIG. 1.

Example 1. Evaluation of Effect of YMJHT on Pharmacokinetics of Metformin: One-Time Oral Co-Administration within 5 Minutes 1.1. Preparation of Laboratory Animals In Example 1, male SD rats (SLC, Japan) were selected as laboratory animals. 500 mg/kg of metformin was orally administered once and then 100 mg/kg of YMJHT was orally administered once within 5 minutes to the rats, blood samples were taken from the rats 30 minutes before the administration, 0.5, 1, 2, 3, 4, 6, 8 and 24 hours after the administration to measure blood metformin concentration, and noncompartmental pharmacokinetics data ($C_{max}$, $T_{max}$, AUC, $t_{1/2}$ and $MRT_{inf}$) were calculated and comparatively analyzed with a metformin single treated group. A total of 10 rats were divided into two groups (a metformin 500 mg/kg single treated group and a metformin+YMJHT 100 mg/kg administered group) for experiments.

1.2. Administration and Blood Sampling Methods 500 mg/kg of metformin was diluted with sterile distilled water, the resultant diluent was orally administered once at a dose of 5 ml/kg, 100 mg/kg of YMJHT was diluted with sterile distilled water within 5 minutes after the metformin treatment, and the resultant diluent was orally administered once at the same dose as used above. Meanwhile, in the metformin single treated group, the same dose of sterile distilled water, instead of YMJHT, was only orally administered once.

Approximately 0.5 ml of whole blood was taken from a retro-orbital plexus using a tube treated with 50 IU of heparin (Sigma, Mo., USA) 30 minutes before the administration, and 0.5, 1, 2, 3, 4, 6, 8 and 24 hours after the administration, and then centrifuged at 13,000 rpm for 10 minutes to separate plasma. The separated plasma was stored at −70° C. before LC-MS/MS analyses. An analysis method for each group is shown in Table 1.

TABLE 1

| | |
|---|---|
| Analysis of blood metformin concentration | The blood metformin concentration in the separated plasma was measured by LC-MS/MS methods using Carbamazepine (Sigma, MO, USA) as an internal standard. Chromatographic analysis was performed using Agilent 1100 Series HPLC (Agilent Technologies, CA, USA), and a column effluent was analyzed using an API 2000 triple-quadruple mass spectrometric detector (Applied Biosystems, Foster City, CA, USA). |
| HPLC conditions | Column: Shiseido CAPCELL PAK ™C18MG-II (2.0 × 150 mm, 5 μm) (Shiseido, Tokyo, Japan) Column oven: not used Mobile phase: 40% distilled water (10 mM $NH_4OAC$, 0.1% formic acid)/60% acetonitrile, Flow rate: 0.20 ml/min, Injection volume: 2.0 μl |
| LC/MS/MS | Ion source: Turbo Ion Spray (375° C.) Polarity: Positive, Multiple reaction monitoring (MRM): Carbamazepine (IS): m/z 237 > 194 (Retention time: 2.5 min), metformin: 130 > 71 (Retention time: 1.3 min) Standard curve: Analyst 1.4.1, Linear (1/x2, no Iterate) |

1.3. Results

Blood metformin concentrations (μg/ml) measured 30 minutes before the administration, and 0.5, 1, 2, 3, 4, 6, 8 and 24 hours after the administration, and pharmacokinetic parameters such as $C_{max}$, $T_{max}$, AUC, $t_{1/2}$ and $MRT_{inf}$ (noncompartmental pharmacokinetics data analyzer program; PK solutions 2.0; Summit, Co., USA) were estimated. Changes in $C_{max}$, $T_{max}$, AUC, $t_{1/2}$ and $MRT_{inf}$ are listed in FIG. 2.

1.3.1. Observation of Blood Metformin Concentration

In the metformin single treated group or the metformin+YMJHT administered group, blood metformin started to be detected from 30 minutes after the drug administration, and was consistently detected until 24 hours after the administration. Insignificant decreases in blood metformin concentration were determined at 2 and 3 hours after the administration, and insignificant increases in blood metformin concentration were determined at 6, 8 and 24 hours after the administration in the metformin+YMJHT administered group, compared with the metformin single treated group. However, a significant change in blood metformin concentration was not detected (FIG. 2).

In the metformin+YMJHT administered group, the blood metformin concentrations detected at 0.5, 1, 2, 3, 4, 6, 8 and 24 hours after the administration changed by −9.24, −6.96, −20.68, −19.27, −11.45, 21.00, 29.48 and 44.69%, respectively, compared with the metformin single treated group.

1.3.2. Change in $T_{max}$ $T_{max}$ change values are shown in Table 2. In the metformin+YMJHT administered group, the $T_{max}$ of metformin in blood was detected at 0.90±0.22 hrs, indicating that the $T_{max}$ of metformin in blood was insignificantly changed by −18.18%, compared with the $T_{max}$ of 1.10±0.55 hrs in the metformin single treated group.

1.3.3. Changes in $C_{max}$

In the metformin+YMJHT administered group, the $C_{max}$ of metformin in blood was 23.24±46.69 μg/ml, indicating that the $C_{max}$ of metformin in blood insignificantly changed by −9.99%, compared with the $C_{max}$ of 25.82±3.08 μg/ml in the metformin single treated group.

1.3.4. Change in AUC

In the metformin+YMJHT administered group, the $AUC_{0-t}$ and $AUC_{0-inf}$ of metformin in blood were 156.57±27.06 and 200.00±29.04 hr·μg/ml, respectively, indicating that the $AUC_{0-t}$ and $AUC_{0-inf}$ of metformin insignificantly changed by 6.05 and 12.96% respectively, compared with the $AUC_{0-t}$ and $AUC_{0-inf}$ of 147.63±24.37 and 177.06±35.17 hr·μg/ml in the metformin single treated group.

1.3.5. Change in $t_{1/2}$

In the metformin+YMJHT administered group, the $t_{1/2}$ of metformin in blood was 9.23±3.23 hrs, indicating that the $t_{1/2}$ of metformin insignificantly increased by 14.36%, compared with the $t_{1/2}$ of 10.56±1.73 hrs in the metformin single treated group.

1.3.6. Change in $MRT_{inf}$

In the metformin+YMJHT administered group, the $MRT_{inf}$ of metformin in blood was 14.44±2.65 hrs, indicating that the $MRT_{inf}$ of metformin insignificantly increased by 27.25%, compared with the $MRT_{inf}$ of 11.35±5.18 hrs in the metformin single treated group.

In Example 1, compared with the metformin single treated group, through the co-administration of YMJHT and metformin once within 5 minutes, significant changes in blood metformin concentration and pharmacokinetic parameters were not observed. Accordingly, it was observed that the co-administration of YMJHT once within 5 minutes did not influence the absorption and excretion of metformin.

Example 2. Evaluation of Influence of Yukmijihwang-Tang on Pharmacokinetics of Metformin: Repeated Oral Co-Administration of Yukmijihwang-Tang and Metformin for 8 Days within 5 Minutes after Repeated Oral Administration of Yukmijihwang-Tang for 6 Days In Example 2, to more precisely evaluate the interaction between YMJHT and metformin than in Example 1, the influence on the pharmacokinetics of metformin after YMJHT was pre-administered repeatedly for 6 days, and then YMJHT was orally co-administered with metformin repeatedly for 8 days within 5 minutes, and the influence on the pharmacokinetics of metformin was also evaluated using male SD rats (SLC, Japan). In Example 2, 100 mg/kg of YMJHT was orally administered once a day for 6 days and then 500 mg/kg of metformin was orally administered for 8 days, blood samples were taken 30 minutes before and 0.5, 1, 2, 3, 4, 6, 8 and 24 hours after the first and last $8^{th}$ metformin administration to measure blood metformin concentrations, and noncompartmental pharmacokinetics data ($C_{max}$, $T_{max}$, AUC, $t_{1/2}$ and MRT) were calculated and comparatively analyzed with those of the metformin single treated group.

2.1. Administration and Blood Sampling Methods 100 mg/kg of YMJHT was diluted with sterile distilled water, and the resultant diluent was orally administered repeatedly once a day for 14 days at a dose of 5 ml/kg, 5 mg/kg of metformin (Wako, Osaka, Japan) was diluted with sterile distilled water 6 days after the first administration of YMJHT, and the resultant diluent was orally administered once for 8 days at a dose of 5 ml/kg. After the pre-administration of YMJHT, in the co-administered group, 100 mg/kg of YMJHT was orally administered within 5 minutes after the metformin administration, and in the metformin single treated group, during the pre-administration and co-administration of YMJHT, instead of YMJHT, the same dose of sterile distilled water was solely administered.

Approximately 0.5 ml of a whole blood sample was taken from the ophthalmic venous plexus using tubes treated with 50 IU of heparin (Sigma, Mo., USA) 30 minutes before and 0.5, 1, 2, 3, 4, 6, 8 and 24 hours after the first and last 8th metformin administration. Right after the taking of the whole blood sample, the whole blood sample was centrifuged at 13,000 rpm for 10 minutes to separate plasma. The separated plasma was stored at −70° C. before LC-MS/MS analyses. An analysis method for each group is shown in Table 1.

2.2. Results

Blood metformin concentrations (μg/ml) 30 minutes before and 0.5, 1, 2, 3, 4, 6, 8 and 24 hours after the first and last 8th metformin administration, and the pharmacokinetic parameters such as $C_{max}$, $T_{max}$, AUC, $t_{1/2}$ and $MRT_{inf}$ (noncompartmental pharmacokinetics data analyzer program; PK solutions 2.0; Summit, Co., USA) were estimated. Changes in $C_{max}$, $T_{max}$, AUC, $t_{1/2}$, and $MRT_{inf}$ were shown in Table 2 (after the first administration) and Table 3 (after the 8th administration).

TABLE 2

| | Metformin (500 mg/kg) | |
| --- | --- | --- |
| Parameters | Without YMJHT co-administration (Distilled water) | With YMJHT co-administration (100 mg/kg) |
| Tmax(hrs) | 0.90 ± 0.22 | 0.90 ± 0.22 |
| Cmax(g/ml) | 20.20 ± 3.42 | 34.80 ± 9.04* |
| $AUC_{0-t}$(hrg/ml) | 126.22 ± 24.71 | 175.50 ± 18.37* |
| $AUC_{0-inf}$(hrg/ml) | 159.94 ± 26.47 | 213.16 ± 32.84* |
| $t_{1/2}$(hr) | 10.72 ± 3.37 | 9.97 ± 1.28 |
| $MRT_{inf}$(hr) | 13.99 ± 4.80 | 11.71 ± 2.80 |

Values are expressed as mean ± SD of five rats

TABLE 3

| | Metformin(500 mg/kg) | |
| --- | --- | --- |
| Parameters | Without YMJHT co-administration (Distill water) | With YMJHTco-administration (100 mg/kg) |
| Tmax(hrs) | 3.00 ± 1.00 | 2.38 ± 2.50 |
| Cmax(g/ml) | 42.20 ± 10.57 | 66.75 ± 30.74* |
| $AUC_{0-t}$(hrg/ml) | 425.14 ± 225.60 | 531.99 ± 181.63 |
| $AUC_{0-inf}$(hrg/ml) | 499.36 ± 211.07 | 612.11 ± 155.90 |
| $t_{1/2}$(hr) | 9.63 ± 4.95 | 8.59 ± 4.09 |
| $MRT_{inf}$(hr) | 12.61 ± 5.86 | 11.44 ± 6.02 |

Values are expressed as mean ± SD of five rats except for YMJHT + metformin repeated treated rats, in which one rat was died after 7th metformin treatment, unfortunately by bad gastric gavages.
YMJHT = Yukmijihwang-tang, purchase from Korea INS Pharm. (Hwasoon, Korea)
Cmax: The peak plasma concentration
Tmax: Time to reach Cmax
$AUC_{0-t}$: The total area under the plasma concentration-time curve from time zero to time measured
$AUC_{0-inf}$: The total area under the plasma concentration-time curve from time zero to time infinity
$t_{1/2}$: half life
$MRT_{inf}$: mean residence to time infinity
*p < 0.05 as compared with metformin single treated rats by MW test 2.2.1. Change in Body Weight In the metformin+YMJHT administered group, compared with the metformin single treated group, significant changes in body weights and body weight gains were not detected during the entire period of the experiment (FIG. 3).

2.2.2. Observation of Blood Metformin Concentration

Figure 4A:
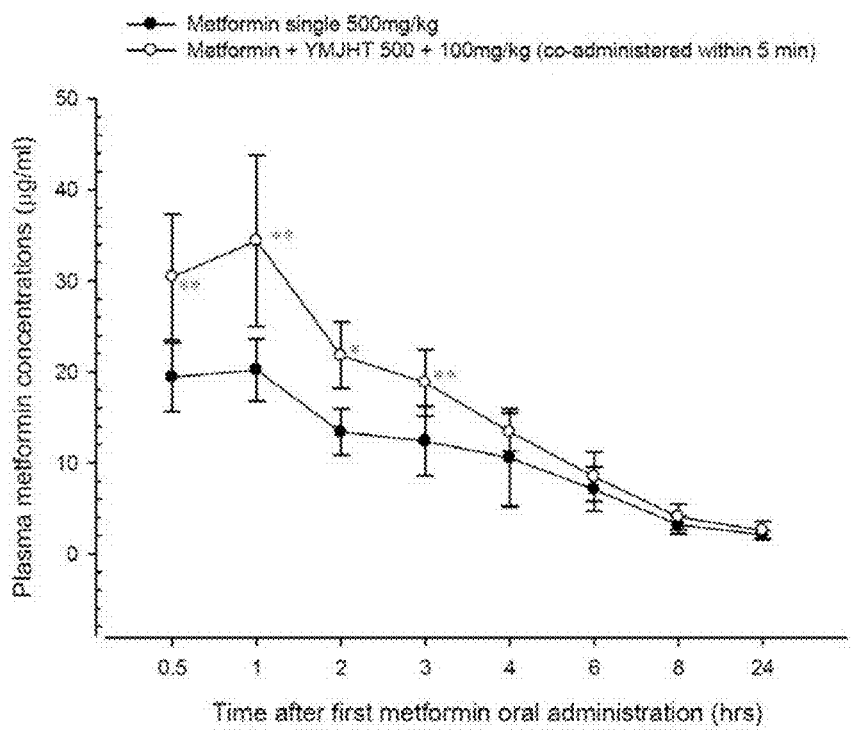
FIG. 4A shows changes in blood metformin concentrations for the metformin single treated group and the group in which only Yukmijihwang-tang is repeatedly oral-administered for 6 days, and then
Figure 4B:
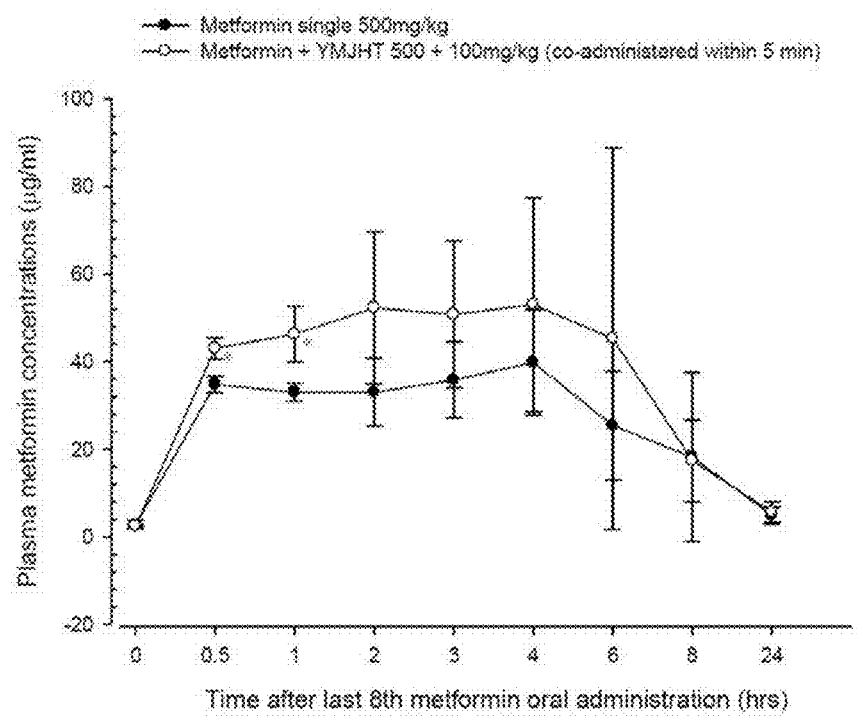
FIG. 4B shows changes in blood metformin concentration when the Yukmijihwang-tang is co-administered within 5 minutes after repeated administration of metformin for 8 days.

In the metformin single treated group or the metformin+YMJHT administered group, metformin in blood started to be detected after the first administration of metformin and 30 minutes after the administration and was detected until 24 hours after the administration, and observed from 30 minutes before administration to 24 hours after administration after the last 8th administration. Also, in the metformin+YMJHT administered groups in which metformin was orally administered once and daily for 8 days after the pre-administration of YMJHT, compared with the metformin single treated group, general increases in blood metformin concentration were shown, and particularly, significant (p<0.01 or p<0.05) increases in content of metformin in blood were observed throughout 0.5 to 3 hours after the first administration of metformin (FIG. 4A), and significant (p<0.05) increases in blood metformin concentration were also observed at 0.5 and 1 hour after the last 8th administration (FIG. 4B).

After YMJHT was pre-administered, followed by the first oral metformin administration, the blood metformin concentrations detected at 0.5, 1, 2, 3, 4, 6, and 8 hours after the administration changed by 56.70, 70.30, 62.93, 51.86, 27.13, 19.44, 26.25 and 21.90% in the metformin+YMJHT co-administered group, respectively, compared with the metformin single treated group.

After metformin was orally co-administered 8 times after pre-administration of YMJHT, the blood metformin concentrations detected at 30 minutes before the administration, 0.5, 1, 2, 3, 4, 6, and 8 hours after the administration changed by −12.14, 23.56, 40.15, 58.33, 41.76, 33.17, 78.15, −4.40 and 16.33% in the metformin+YMJHT co-administered group, respectively, compared with the metformin single treated group.

2.2.3. Change in $T_{max}$

As shown in Tables 2 and 3, after pre-administration of YMJHT, followed by the first oral administration of metformin, the $T_{max}$ of metformin in blood was detected at 0.90±0.22 hrs in the metformin+YMJHT administered group, and was also detected at 0.90±0.00 hrs in the metformin single treated group. After pre-administration of YMJHT, followed by 8 times of repeated orally co-administration of YMJHT, the $T_{max}$ of metformin in blood was 2.38±2.50 hrs in the metformin+YMJHT administered group, indicating that the $T_{max}$ of metformin in blood insignificantly changed by −20.83%, compared with the $T_{max}$ of 3.00±1.00 hrs in the metformin single treated group.

2.2.4. Change in $C_{max}$

As shown in Tables 2 and 3, after pre-administration of YMJHT, followed by the first oral administration of metformin, the $C_{max}$ of metformin in blood was 34.80±9.04 µg/ml in the metformin+YMJHT co-administered group, indicating that the $C_{max}$ of metformin in blood significantly (p<0.05) changed by 72.28%, compared with the $C_{max}$ of 20.20±3.42 µg/ml in the metformin single treated group. Even after metformin was repeatedly orally co-administered 8 times after pre-administration of YMJHT, the $C_{max}$ of metformin in blood was 66.75±30.74 µg/ml in the metformin+YMJHT co-administered group, indicating that the $C_{max}$ of metformin in blood insignificantly changed by 58.18%, compared with the $C_{max}$ of 42.20±10.57 µg/ml in the metformin single treated group.

2.2.5. Change in AUC

As shown in Tables 2 and 3, after pre-administration of YMJHT, followed by the first oral administration of metformin, the $AUC_{0-t}$ and $AUC_{0-inf}$ of metformin in blood were 175.50±18.37 and 213.16±32.84 hr·m/ml, respectively, in the metformin+YMJHT administered group, indicating that the $AUC_{0-t}$ and $AUC_{0-inf}$ of metformin in blood were significantly (p<0.05) changed by 39.04 and 33.27%, respectively, compared with the $AUC_{0-t}$ and $AUC_{0-inf}$ of 126.22±24.71 and 159.94±26.47 hr·m/ml in the metformin single treated group. Even after metformin was repeatedly orally co-administered 8 times after pre-administration of YMJHT, the $AUC_{0-t}$ and $AUC_{0-inf}$ of metformin in blood were detected at 531.99±181.63 and 612.11±155.90 hr·m/ml, respectively, in the metformin+YMJHT administered group, indicating that the $AUC_{0-t}$ and $AUC_{0-inf}$ of metformin insignificantly changed by 25.13 and 22.58%, compared with the $AUC_{0-t}$ and $AUC_{0-inf}$ of 425.14±225.60 and 499.36±211.07 hr·m/ml in the metformin single treated group (Tables 2 and 3).

2.2.6. Change in $t_{1/2}$

After pre-administration of YMJHT, followed by the first oral administration of metformin, the $t_{1/2}$ of metformin in blood was 9.97±1.28 hr in the metformin+YMJHT administered group, indicating that the $t_{1/2}$ of metformin in blood insignificantly changed by −6.95%, compared with the $t_{1/2}$ of 10.72±3.37 hr in the metformin single treated group. Even after metformin was repeatedly orally co-administered 8 times after pre-administration of YMJHT, the $t_{1/2}$ of metformin in blood was 8.59±4.09 hr in the metformin+YMJHT administered group, indicating that the $t_{1/2}$ of metformin in blood insignificantly changed by −10.75%. compared with the $t_{1/2}$ of 9.63±4.95 hr in the metformin single treated group (Tables 2 and 3).

2.2.7. Change in $MRT_{inf}$

After pre-administration of YMJHT, followed by the first oral administration of metformin, the $MRT_{inf}$ of metformin in blood was 11.71±2.80 hr in the metformin+YMJHT administered group, indicating that the $MRT_{inf}$ of metformin in blood insignificantly changed by −16.25%, compared with the $MRT_{inf}$ of 13.99±4.80 hr in the metformin single treated group. Even after the pre-administration of YMJHT, followed by repeated oral co-administration of metformin 8 times, the $MRT_{inf}$ of metformin in blood was 11.44±6.02 hr in the metformin+YMJHT administered group, indicating that the $MRT_{inf}$ of metformin in blood insignificantly changed by −9.22%, compared with the $MRT_{inf}$ of 12.61±5.86 hr in the metformin single treated group.

According to the result of Example 2, different from that of Example 1, after pre-administration of YMJHT, followed by the first oral administration of metformin, in the metformin+YMJHT administered group, compared with the metformin single treated group, a significant increase (p<0.01 or p<0.05) in blood metformin concentration was observed from 30 minutes to 3 hours after the administration, significant increases (p<0.05) in $C_{max}$ (72.28%), $AUC_{0-t}$ (39.04%) and $AUC_{0-inf}$ (33.27%) were observed. Even after the repeated administration 8 times, in the metformin+YMJHT administered group, compared with the metformin single treated group, a significant increase (p<0.05) in blood metformin concentration was observed 30 minutes and 1 hour after the administration, but significance was not observed with the significant increase (p<0.05) in $C_{max}$ (58.18%), and significant increases in $AUC_{0-t}$ (25.13%) and $AUC_{0-inf}$ (22.58%) were shown.

Accordingly, it was observed that the repeated pre-treatment of YMJHT and repeated co-administration of YMJHT and metformin within 5 minutes led to a considerable increase in absorption of metformin, thereby increasing oral bioavailability, and to provide an effective treating method for diabetes, it is determined that the influence on the pharmacokinetics of metformin has to be evaluated after the co-administration of metformin at intervals of $T_{max}$ or more, that is, two hours.

Example 3. Experiment of Co-Administration of Yukmijihwang-Tang and Metformin: Influence of Yukmijihwang-Tang on Effect of Metformin in Streptozotocin (STZ)-Induced Type I Diabetes Rats Combining the results of Example 1 and Example 2, it was found that YMJHT had no significant influence on absorption and excretion of metformin, that is, oral bioavailability, when the YMJHT and metformin were orally co-administered once within 5 minutes, and the bioavailability was increased through the considerable increase in absorption of metformin in all of the repeated pre-administration of YMJHT and the repeated oral administration with metformin within 5 minutes. Accordingly, in Example 3, to examine the influence of the YMJHT and metformin co-administration on an antidiabetic effect, a representative Type I diabetes laboratory animal model, that is, STZ-induced diabetes rat was used. As the laboratory animals, Sprague-Dawley (SD), Slc:SD rats (6-week-old females, SLC, Shizuoka, Japan) were used, an experiment method was briefly illustrated in FIG. 5A, and the design of experimental groups is shown in FIG. 5B.

105 SD rats were purchased, and 21 days after STZ administration, only rats having uniform body weights (12~180 g) and blood sugar levels (257~358 mg/dl) were selected. Among those, 8 rats per group were used in the experiment, and separate 8 rats were also prepared as the intact vehicle control (body weight: 200~262 g; blood sugar level: 88~100 mg/dl).

STZ was diluted with 50 mM citrate buffer (pH 6.0), and the resultant diluent was peritoneally administered once at a dose of 60 mg/kg/5 ml to induce diabetes, and in the intact vehicle control, instead of STZ, the same dose of citrate buffer was solely administered in the same route. From 22 days after the STZ administration, 400, 200 or 100 mg/kg of YMJHT was co-administered with 500 mg/kg of metformin at 2-hour intervals daily for 28 days, and in the YMJHT or metformin single treated group, only the same dose of sterile distilled water was administered, and in the vehicle control, only sterile distilled water was administered as a vehicle twice at 2-hour intervals.

Observation Items

The items observed included, for example, an antidiabetic effect, liver and kidney protecting effects, an antihyperlipidemic effect, immune activity and an ocular protecting effect:

(1) Change in body weight: Body weight gains during diabetes induction and administration of a candidate material for 28 days (2) Antidiabetic effect: Change in blood sugar level, morphological change in pancreas tissue—changes in the number and diameter of pancreatic islets, and numerical changes in insulin and glucagon immunoreactive cells (3) Liver protecting effect: changes in the liver weight, blood AST and ALT contents, histopathological findings on the liver—(Degeneration rate of the liver: ratio of degenerated liver cells per $mm^2$ of hepatocyte, number of liver cells: number of liver cells observed per $mm^2$ of hepatocyte).

(4) Kidney protecting effect: kidney weights, changes in blood BUN and creatinine, histopathological findings on kidney—numbers of degenerated renal tubules and glomeruli (5) Antihyperlipidemic effect: changes in blood triglyceride, total cholesterol, LDL, HDL contents (6) Immune activity effect: thymus and spleen weights and histopathological findings—changes in spleen thickness, the number of white pulps and diameter, changes in thymus lobules and cortex thicknesses (7) Ocular protecting effect: observer-based and quantitative image scorings for cataract, histopathological change of ocular—ocular lens damage scores, retina thickness, thicknesses of an inner plexiform layer and inner nuclear layer of the retina, numerical change in blood vessels present in the retina (8) Change in antioxidative defense system in kidney: lipid peroxidation in kidney (nM of malondialdehyde (MDA)/g protein), endogenous antioxidant—glutathione (GSH) content (nM/g protein), antioxidant enzyme—Changes in catalase and superoxide dismutase (SOD) activities (U/mg protein)

To clarify degrees of inducing diabetes and diabetic complications, blood sugar levels was measured at 21 days after the STZ administration and 28 days after the administration of a candidate material, and then a difference between them was estimated. Also, to minimize a difference between organ weights depending on a body weight, an absolute weight was measured, and then a ratio to the body weight, that is, a relative weight, was calculated.

3.1. Changes in Body Weight and Body Weight Gain

Figures 6A, 6B:
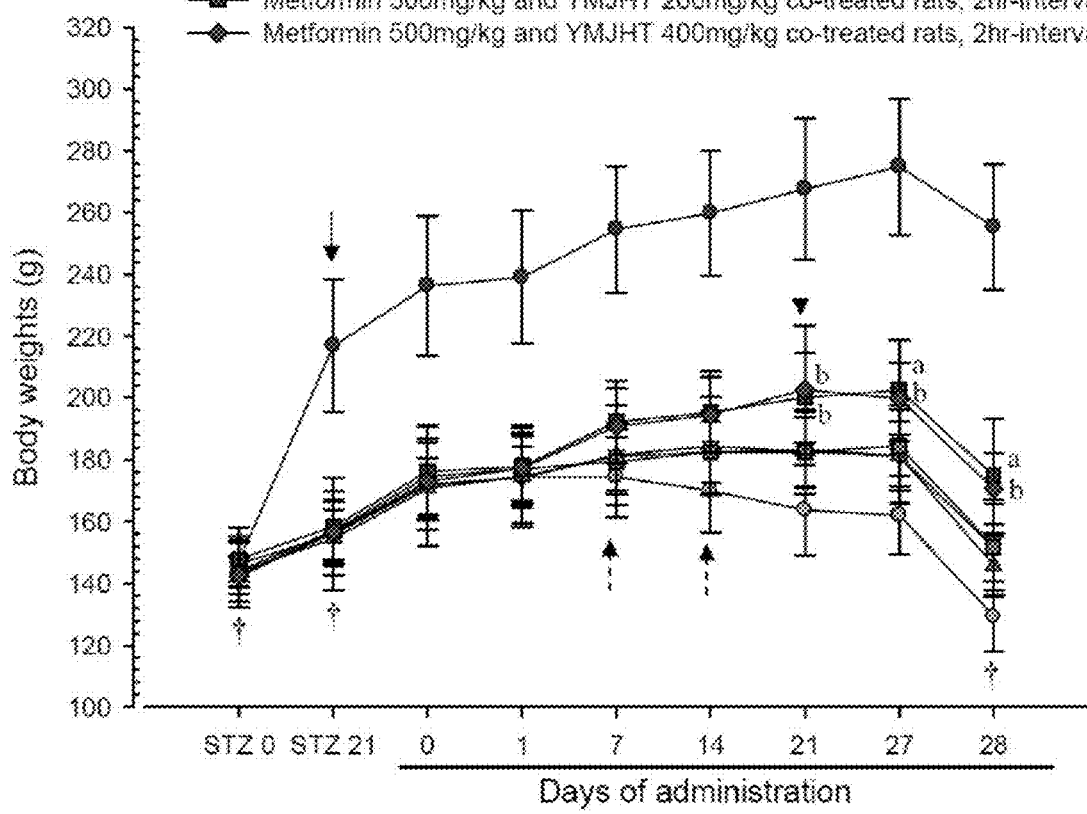
FIGS. 6A and 6B show changes in body weights and body weight gains by group.

Since laboratory animals that were uniformly decreased in body weight, compared with the vehicle control, 21 days after the STZ administration were selected and used, a significant decrease (p<0.01) in body weight started to be detected from 21 days after the STZ administration in the STZ control, compared with the intact vehicle control, and body weight gains during the three-week induction and 28-day administration were also significantly decreased (p<0.01), compared with the intact vehicle control. Meanwhile, in the metformin 500 mg/kg or YMJHT 400 mg/kg single treated group and the YMJHT 100, 200 or 400 mg/kg and metformin 500 mg/kg co-administered group, compared with the STZ control, significant (p<0.01 or p<0.05) increases in body weights started to be detected from 7 or 21 days after the administration, and body weight gains during the administration were also significantly increased (p<0.01) in all of the administered groups, compared with the STZ control. Particularly, in the YMJHT 200 or 400 mg/kg and metformin co-administered group, compared with the metformin single treated group, a significant increase (p<0.01) in body weight started to be detected from 21 days after the administration, and compared with the metformin 500 mg/kg administered group, the body weight gain during the administration was also significantly increased (p<0.01) (FIGS. 6A and 6B).

Body weight gains during the diabetes induction changed by −86.18% in the STZ control, compared with the intact vehicle control, and changed by 45.45, 12.99, 35.06, 9.09, 45.45 and 45.45% in the metformin 500 mg/kg and YMJHT 400 mg/kg single treated groups, and the YMJHT 100, 200 and 400 mg/kg and metformin 500 mg/kg co-administered groups, respectively compared with the STZ control.

Body weight gains during the 28-day administration of an experiment material changed by −125.32% in the STZ control, compared with the intact vehicle control, and changed by 193.31, 209.97, 202.28, 370.23 and 375.36% in the metformin 500 mg/kg and YMJHT 400 mg/kg single treated groups, and the YMJHT 100, 200 and 400 mg/kg and metformin 500 mg/kg co-administered groups, respectively, compared with the STZ control.

As seen from the above results, after the STZ administration, a considerable decrease in body weight was detected, but the decrease in body weight through the STZ administration was considerably suppressed by all of the administrations of metformin and YMJHT, and particularly, in the YMJHT 400 and 200 mg/kg co-administered groups at 2-hour intervals, compared with the metformin single treated group, significant increases (p<0.01 or p<0.05) in body weight and body weight gain were detected. Such results show that an antidiabetic effect of metformin and a metformin effect on diabetic complications were considerably increased through the YMJHT co-administration.

3.2. Antidiabetic Effect
3.2.1. Change in Blood Sugar Level 21 days after STZ administration, in all of the STZ administered groups, compared with the intact vehicle control, significant increases (p<0.01) in blood sugar level were detected, and in the STZ control, even 28 days after the administration, compared with the intact vehicle control, significant increases (p<0.01) were detected. Blood sugar variations during the 28-day administration were also significantly increased (p<0.01), compared with the intact vehicle control. Meanwhile, in the metformin and YMJHT single treated groups and all three doses of YMJHT and metformin co-administered groups, compared with the STZ control, significant decreases (p<0.01 or p<0.05) in blood sugar levels were detected after the end of the administration, and blood sugar variations during the administration were also considerably decreased in all of the administered groups, compared with the STZ control. Particularly, in the YMJHT 200 and 400 mg/kg and metformin co-administered groups, compared with the metformin single treated group, significant decreases (p<0.01 or p<0.05) in blood sugar levels after the end of the administration and blood sugar variations during the administration were detected (FIG. 7A).

The blood sugar level at 21 days after the STZ administration changed by 216.05% in the STZ control, compared with the intact vehicle control, and changed by 1.68, −0.34, −1.30, −0.04 and 0.08% in the metformin 500 mg/kg and YMJHT 400 mg/kg single treated groups, and the YMJHT 100, 200 and 400 mg/kg and metformin 500 mg/kg co-administered groups, respectively, compared with the STZ control.

The blood sugar level at 28 days after the STZ administration changed by 442.93% in the STZ control, compared with the intact vehicle control, and changed by −27.25, −18.84, −29.33, −39.53 and −47.26% in the metformin 500 mg/kg and YMJHT 400 mg/kg single treated groups, and the YMJHT 100, 200 and 400 mg/kg and metformin 500 mg/kg co-administered groups, respectively, compared with the STZ control.

The blood sugar variation from 21 days after the STZ administration to 28 days after the administration of a candidate material changed by 2581.25% in the STZ control, compared with the intact vehicle control, and changed by −59.39, −39.39, −60.47, −83.40 and −99.86% in the metformin 500 mg/kg and YMJHT 400 mg/kg single treated groups, and the YMJHT 100, 200 and 400 mg/kg and metformin 500 mg/kg co-administered groups, respectively, compared with the STZ control.

As seen from the above results, when the final necropsy was carried out on each of 21 days after the STZ administration and 28 days after the drug administration, in all of the STZ-administered rats, considerable increases in blood sugar levels were detected, but the increase in blood sugar level through the STZ administration was considerably suppressed by all of the administrations of metformin and YMJHT. Particularly, in the YMJHT 400 and 200 mg/kg co-administered groups, compared with the metformin single treated group, significant decreases (p<0.01 or p<0.05) in blood sugars were detected. Through such results, it was seen that a hypoglycemic effect of metformin was considerably increased through the co-administration of YMJHT.

3.2.2. Change in Pancreas Weight

Except that the significant decrease (p<0.05) only was shown in the YMJHT single treated group, in all STZ treated groups, compared with the intact vehicle control, significant changes in absolute weights of the pancreas were not detected, and compared with the intact vehicle control, secondary significant increases (p<0.01) in relative weights of the pancreas caused by the decrease in body weight were detected in all of STZ-induced diabetes groups.

Meanwhile, in the YMJHT single treated group, and the YMJHT 200 and 400 mg/kg and metformin co-administered groups, compared with the STZ control, significant decreases (p<0.01 or p<0.05) in relative weights of the pancreas were detected, and in all of the YMJHT and metformin co-administered groups, compared with the metformin 500 mg/kg single treated group, significant changes in pancreas weights were not detected (FIG. 7B).

Pancreas absolute weights changed by −9.92% in the STZ control, compared with the intact vehicle control, and changed by 7.95, −2.49, 7.21, 9.65 and 12.07% in the metformin 500 mg/kg and YMJHT 400 mg/kg single treated groups, and the YMJHT 100, 200 and 400 mg/kg and metformin 500 mg/kg co-administered groups, respectively, compared with the STZ control.

Relative pancreas weights with respect to the body weight on the final sacrifice day changed by 78.77% in the STZ control, compared with the intact vehicle control, and changed by −7.49, −13.34, −8.21, −18.10 and −14.70% in the metformin 500 mg/kg and YMJHT 400 mg/kg single treated groups, and YMJHT 100, 200 and 400 mg/kg and metformin 500 mg/kg co-administered groups, respectively, compared with the STZ control.

3.2.3. Histopathological Change in Pancreas

In the STZ control, compared with the intact vehicle control, considerable numerical decreases in pancreatic islets were detected along with the contraction of the pancreatic islet, the number of pancreatic islets per 100 $mm_2$ of a pancreatic parenchyma was significantly decreased (p<0.01), compared with the intact vehicle control, and a mean diameter of the pancreatic islet was also significantly decreased (p<0.01), compared with the intact vehicle control. Meanwhile, in all of the metformin and YMJHT single treated groups, and the metformin and YMJHT co-administered groups, compared with the STZ control, significant increases (p<0.01) in the number of pancreatic islets and mean diameter were shown. Particularly, in the YMJHT 200 and 400 mg/kg and metformin co-administered groups, compared with the metformin single treated group, significant increases (p<0.01 or p<0.05) in the number of pancreatic islets and mean diameter were detected (FIG. 7C).

Numbers of pancreatic islets per unit area changed by −75.57% in the STZ control, compared with the intact vehicle control, and changed by 120.93, 93.02, 100.00, 172.09 and 253.49% in the metformin 500 mg/kg and YMJHT 400 mg/kg single treated groups, and the YMJHT 100, 200 and 400 mg/kg and metformin 500 mg/kg co-administered groups, respectively, compared with the STZ control.

Mean diameters of the pancreatic islets changed by −74.49% in the STZ control, compared with the intact vehicle control, and changed by 97.80, 92.73, 101.55, 168.70 and 212.28% in the metformin 500 mg/kg and YMJHT 400 mg/kg single treated groups, and the YMJHT 100, 200 and 400 mg/kg and metformin 500 mg/kg co-administered groups, respectively, compared with the STZ control.

3.2.4. Change in Insulin Immunoreactive Cells

Figure 8:
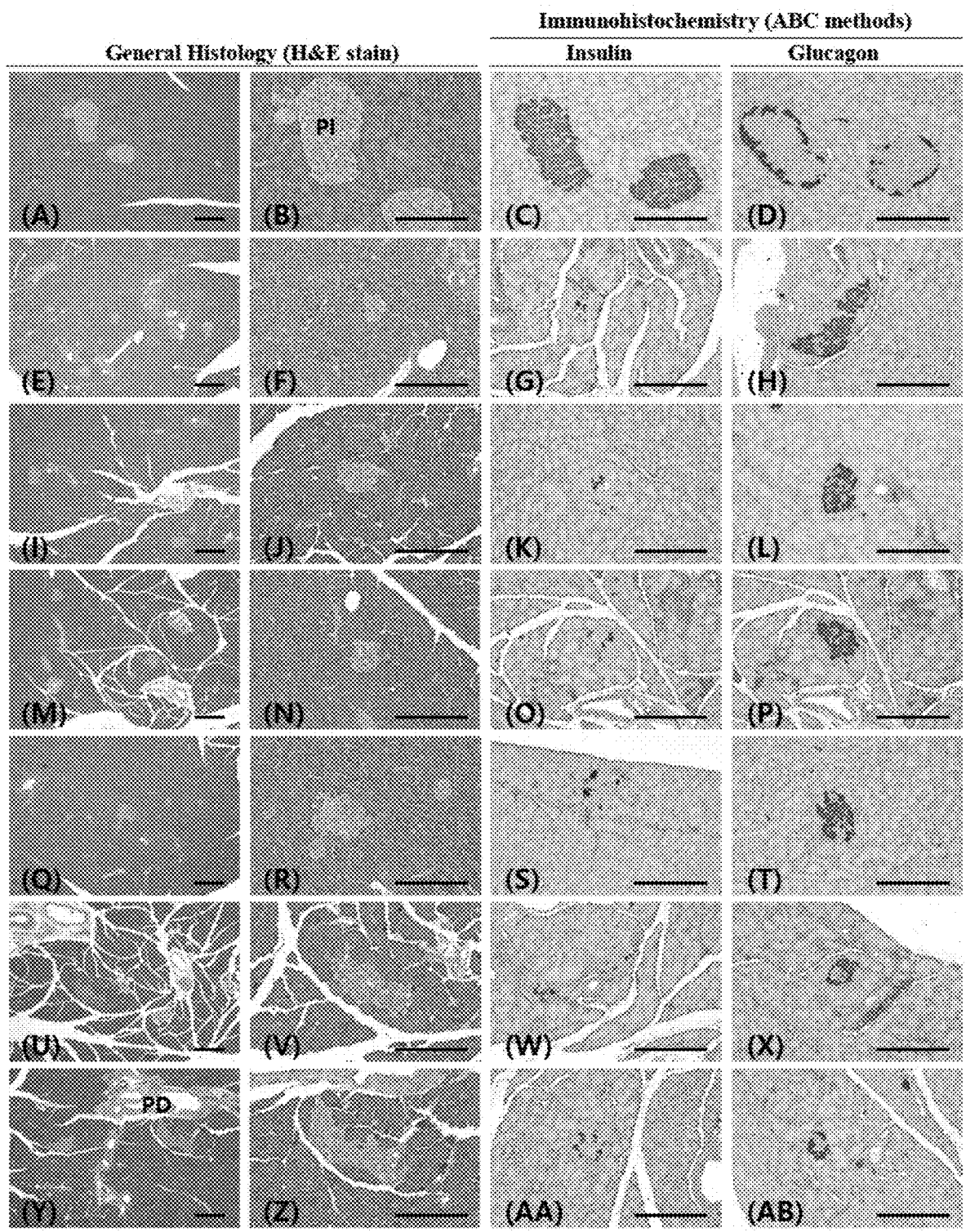
FIG. 8 shows histopathological changes of a pancreas, and numerical changes in insulin immunoreactive cells and glucagon immunoreactive cells through the Yukmijihwang-tang co-administration.

A considerable numerical decrease in insulin immunoreactive cells in the pancreatic islet were shown in the STZ control, compared with the intact vehicle control, and a significant decrease (p<0.01) in the number of insulin immunoreactive cells per unit area (mm²) was shown, compared with the intact vehicle control. However, in all administered groups, compared with the STZ control, a significant numerical increase (p<0.01) in insulin immunoreactive cells was shown, and particularly, in the YMJHT 200 and 400 mg/kg and metformin co-administered groups, compared with the metformin single treated group, significant numerical increases (p<0.01 or p<0.05) in insulin immunoreactive cells per unit area were detected (FIGS. 7C and 8).

Numbers of insulin immunoreactive cells in the pancreatic islet changed by −94.63% in the STZ control, compared with the intact vehicle control, and changed by 202.99, 158.58, 175.00, 320.52 and 541.12% in the metformin 500 mg/kg and YMJHT 400 mg/kg single treated groups, and the YMJHT 100, 200 and 400 mg/kg and metformin 500 mg/kg co-administered groups, respectively, compared with the STZ control.

3.2.5. Change in Glucagon Immunoreactive Cells

A considerable numerical increase in glucagon immunoreactive cells in the pancreatic islet in the STZ control was shown, compared with the intact vehicle control, and a significant increase (p<0.01) in number of glucagon immunoreactive cells per unit area (mm²), compared with the intact vehicle control, was shown. In all administered groups, compared with the STZ control, significant numerical decreases (p<0.01) in glucagon immunoreactive cells were shown, and particularly, in the YMJHT 200 and 400 mg/kg and metformin co-administered groups, compared with the metformin single treated group, significant numerical decreases (p<0.01) in glucagon immunoreactive cells per unit area were detected (FIGS. 7C and 8).

Numbers of the glucagon immunoreactive cells in the pancreatic islet changed by 425.52% in the STZ control, compared with the intact vehicle control, and changed by −27.78, −25.42, −27.95, −49.20 and −59.21% in the metformin 500 mg/kg and YMJHT 400 mg/kg single treated groups, YMJHT 100, 200 and 400 mg/kg and metformin 500 mg/kg co-administered groups, respectively, compared with the STZ control.

As seen from the above results, a decrease in the mean diameter, that is, contraction, was detected in the STZ control, along with the numerical decrease in pancreatic islets, and a numerical increase in glucagon immunoreactive cells was detected along with the numerical decrease in insulin immunoreactive cells in the pancreatic islet. However, such a morphological change of the pancreas and the numerical changes in insulin and glucagon immunoreactive cells were considerably suppressed through all of the metformin or YMJHT administrations. Particularly, in the YMJHT 400 and 200 mg/kg co-administered groups, compared with the metformin single treated group, along with the significant increases (p<0.01 or p<0.05) in the number and diameter of the pancreatic islets, and number of the insulin immunoreactive cells in the pancreatic islet, numerical decreases in glucagon immunoreactive cells were detected. Such results are considered direct evidence of a considerable increase in the antidiabetic effect of metformin, particularly, a protecting effect on insulin producing cells in the pancreatic islet, which is caused by YMJHT co-administration.

3.3. Liver Protecting Effect 3.3.1. Change in Liver Weight

Significant increases (p<0.01) in absolute and relative weights of the liver were detected in the STZ control, compared with the intact vehicle control, but significant decreases (p<0.01) in absolute and relative weights of the liver were not detected in all of the drug administered groups, compared with the STZ control, and particularly, significant decreases (p<0.01 or p<0.05) in relative weight of the liver were detected in the YMJHT 200 and 400 mg/kg and metformin co-administered groups, compared with the metformin single treated group (FIG. 9B).

The absolute weight of the liver changed by 39.44% in the STZ control, compared with the intact vehicle control, and changed by −14.38, −13.09, −13.35, −14.67 and −19.32% in the metformin 500 mg/kg and YMJHT 400 mg/kg single treated groups, and the YMJHT 100, 200 and 400 mg/kg and metformin 500 mg/kg co-administered groups, respectively, compared with the STZ control.

The relative weight of the liver changed by 178.56% in the STZ control, compared with the intact vehicle control, and changed by −27.69, −23.57, −26.88, −37.07 and −39.40% in the metformin 500 mg/kg and YMJHT 400 mg/kg single treated groups, and the YMJHT 100, 200 and 400 mg/kg and metformin 500 mg/kg co-administered groups, respectively, in the STZ control.

3.3.2. Change in Blood AST Content

Significant increases (p<0.01) in blood AST and ALT contents were detected in the STZ control, compared with the intact vehicle control, but significant decreases (p<0.01) in blood AST and ALT contents were detected in the metformin or YMJHT administered group, compared with the STZ control. Particularly, significant decreases (p<0.01 or p<0.05) in blood AST and ALT contents were detected in the YMJHT 200 and 400 mg/kg and metformin co-administered groups, compared with the metformin single treated group (FIG. 9A).

The blood AST content changed by 984.69% in the STZ control, compared with the intact vehicle control, and changed by −32.82, −49.11, −39.47, −55.83 and −72.05% in the metformin 500 mg/kg and YMJHT 400 mg/kg single treated groups, and the YMJHT 100, 200 and 400 mg/kg and metformin 500 mg/kg co-administered groups, compared with the STZ control.

The blood ALT content changed by 1024.30% in the STZ control, compared with the intact vehicle control, and changed by −32.72, −48.32, −37.57, −58.71 and −71.49% in the metformin 500 mg/kg and YMJHT 400 mg/kg single treated groups, and the YMJHT 100, 200 and 400 mg/kg and metformin 500 mg/kg co-administered groups, compared with the STZ control.

3.3.3. Histopathological Change in Liver

Figure 10:
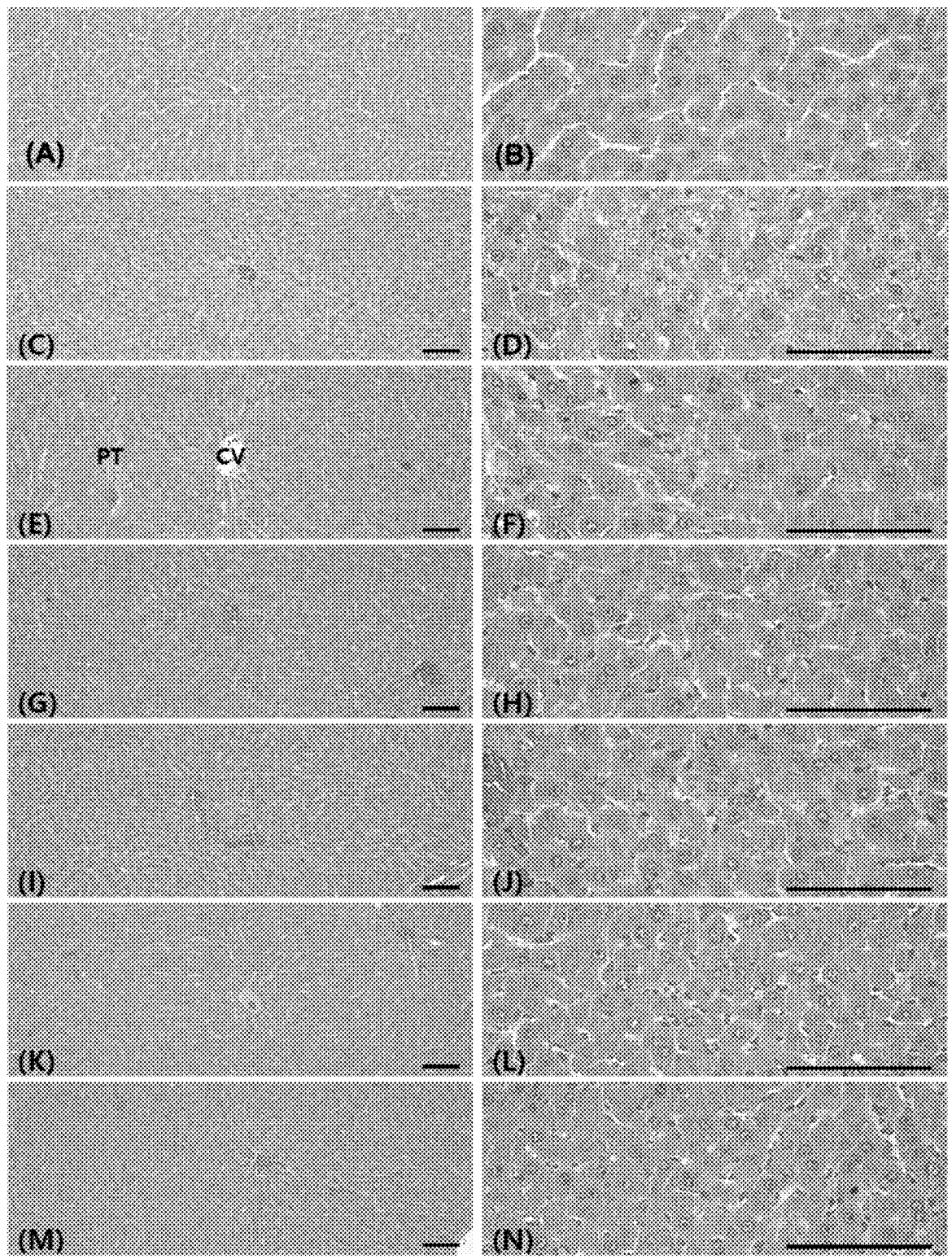
FIG. 10 shows histopathological changes in the liver through the Yukmijihwang-tang co-administration.

In the STZ control, compared with the normal vehicle control, considerable damage characterized by contraction and necrosis of the hepatocytes were observed, and thus a significant increase (p<0.01) in the hepatic degeneration rate and a significant decrease (p<0.01) in the number of hepatocytes per unit area (mm²) were shown. Meanwhile, in all of the administered groups, compared with the STZ control, a significant decrease (p<0.01) in the hepatic degeneration rate and an increase in hepatocytes per unit area were detected. Particularly, in all of the co-administered groups, compared with the metformin single treated group, significant decreases (p<0.01 or p<0.05) in the hepatic degeneration rate were shown, and in the YMJHT 200 and 400 mg/kg and metformin co-administered groups, compared with the metformin single treated group, significant increases (p<0.01 or p<0.05) in hepatocytes per unit area (mm2) were shown (FIGS. 9B and 10).

The hepatic degeneration rate changed by 1254.52% in the STZ control, compared with the intact vehicle control, and changed by −29.61, −39.62, −41.08, −57.33 and −74.07% in the metformin 500 mg/kg and YMJHT 400 mg/kg single treated groups, and the YMJHT 100, 200 and 400 mg/kg and metformin 500 mg/kg co-administered groups, respectively, compared with the STZ control.

The number of mean hepatocytes per unit area changed by −65.89% in the STZ control, compared with the intact vehicle control, and changed by 60.58, 72.73, 79.34, 108.20 and 125.24% in the metformin 500 mg/kg and YMJHT 400 mg/kg single treated groups, and YMJHT 100, 200 and 400 mg/kg and metformin 500 mg/kg co-administered groups, respectively, compared with the STZ control.

As seen from the above results, in all of the STZ administered groups, considerable decreases in degeneration of hepatocytes and related decreases in the number of hepatocytes per unit area were detected along with the considerable increases in liver weight, blood AST and ALT contents, STZ-induced hepatic degeneration was considerably suppressed through all of the administrations of candidate materials, and particularly, in the YMJHT 400 and 200 mg/kg co-administered groups, compared with the metformin single treated group, a significant increase (p<0.01 or p<0.05) in the liver protecting effect was detected. Such a result is considered direct evidence of the considerable increase in the liver protecting effect of metformin through the YMJHT co-administration.

3.4. Kidney protecting effect 3.4.1. Change in kidney weight

Significant increases (p<0.01) in absolute and relative weights of the kidney were detected in the STZ control, compared with the intact vehicle control, but significant decreases (p<0.01) in kidney weights were detected in all of the drug administered groups, compared with the STZ control. Particularly, in the YMJHT 400 mg/kg and metformin co-administered group, compared with the metformin single treated group, significant decreases (p<0.01 or p<0.05) in absolute and relative weight of the kidney were detected, and in the YMJHT 200 mg/kg and metformin co-administered group, compared with the metformin single treated group, a significant decrease (p<0.05) in relative weight of the kidney, and an insignificant decrease in absolute weight of the kidney were detected (FIG. 11B)

The absolute weight of the kidney changed by 68.13% in the STZ control, compared with the intact vehicle control, and changed by −21.29, −15.59, −19.32, −22.70 and −30.65% in the metformin 500 mg/kg and YMJHT 400 mg/kg single treated groups, and in the YMJHT 100, 200 and 400 mg/kg and metformin 500 mg/kg co-administered groups, respectively, compared with the STZ control.

The relative weight of the kidney changed by 233.64% in the STZ control, compared with the intact vehicle control, and changed by −32.41, −25.10, −30.97, −42.54 and −47.48% in the metformin 500 mg/kg and YMJHT 400 mg/kg single treated groups, and the YMJHT 100, 200 and 400 mg/kg and metformin 500 mg/kg co-administered groups, respectively, compared with the STZ control.

3.4.2. Changes in Blood Creatinine and BUN Contents

Significant increases (p<0.01) in blood creatinine and BUN contents were detected in the STZ control, compared with the intact vehicle control, but significant decreases (p<0.01) in blood creatinine and BUN contents were detected in all of the metformin or YMJHT administered groups, compared with the STZ control. Particularly, in the YMJHT 200 and 400 mg/kg and metformin co-administered groups, compared with the metformin single treated group, significant decreases (p<0.01) in blood creatinine and BUN contents were detected (FIG. 11A).

The blood BUN content changed by 395.51% in the STZ control, compared with the intact vehicle control, and changed by −31.69, −34.80, −34.28, −54.85 and −71.93% in the metformin 500 mg/kg and YMJHT 400 mg/kg single treated groups, and the YMJHT 100, 200 and 400 mg/kg and metformin 500 mg/kg co-administered groups, respectively, compared with the STZ control.

The blood creatinine content changed by 177.36% in the STZ control, compared with the intact vehicle control, and changed by −31.29, −35.37, −39.46, −46.26 and −55.78% in the metformin 500 mg/kg and YMJHT 400 mg/kg single treated groups, and the YMJHT 100, 200 and 400 mg/kg and metformin 500 mg/kg co-administered groups, respectively, compared with the STZ control.

3.4.3. Histopathological Change in Kidney

Figure 12:
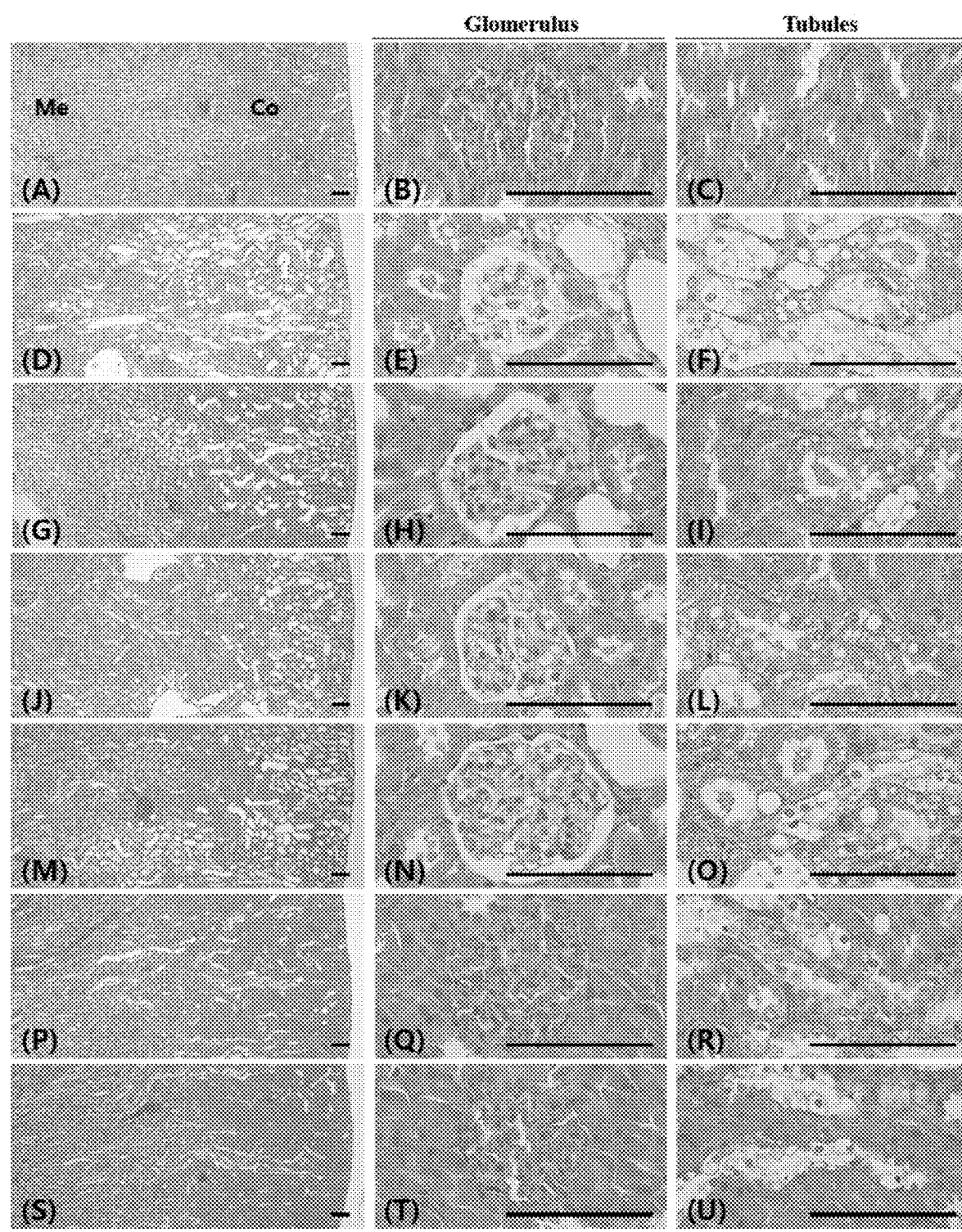
FIG. 12 shows histopathological changes in the kidney.

In the STZ control, compared with the intact vehicle control, kidney degeneration characterized by considerably contracted glomeruli caused by hemotelangiosis and vacuolated renal tubules was observed, and compared with the intact vehicle control, significant numerical increases (p<0.01) in degenerated glomeruli and renal tubules were detected. However, in all of the administered groups, compared with the STZ control, significant numerical decreases (p<0.01) in degenerated glomeruli and renal tubules were detected, and particularly, in the YMJHT 200 and 400 mg/kg and metformin co-administered groups, compared with the metformin single treated group, significant numerical decreases (p<0.01) in degenerated glomeruli and renal tubules were detected (FIGS. 11B and 12).

The number of degenerated glomeruli changed by 3656.25% in the STZ control, compared with the intact vehicle control, and changed by −36.94, −33.11, −37.10, −68.72 and −84.86% in the metformin 500 mg/kg and YMJHT 400 mg/kg single treated groups, and the YMJHT 100, 200 and 400 mg/kg and metformin 500 mg/kg co-administered groups, respectively, compared with the STZ control.

The number of degenerated renal tubules changed by 1119.61% in the STZ control, compared with the intact vehicle control, and changed by −29.90, −33.12, −29.42, −64.95 and −76.85% in the metformin 500 mg/kg and YMJHT 400 mg/kg single treated groups, and the YMJHT 100, 200 and 400 mg/kg and metformin 500 mg/kg co-administered groups, respectively, compared with the STZ control.

As seen from the above results, in the STZ control, kidney weights, numerical changes in contracted glomeruli caused by hemotelangiosis and vacuolated renal tubules were detected along with the increases in blood BUN and creatinine contents, and STZ-induced kidney degeneration was considerably suppressed through all of the metformin or YMJHT administration. Particularly, in the YMJHT 400 and 200 mg/kg co-administered groups, compared with the metformin single treated group, significant increases (p<0.01 or p<0.05) in kidney protecting effect were detected. Such results are considered direct evidences of the considerable increase in kidney protecting effect of metformin through the YMJHT co-administration.

3.5. Antihyperlipidemic Effect 3.5.1. Change in Total Cholesterol and Triglyceride Contents in Blood In the STZ control, compared with the intact vehicle control, significant increases (p<0.01) in total cholesterol and triglyceride contents in blood were detected, and in all of the metformin or YMJHT administered groups, compared with the STZ control, significant decreases (p<0.01) in total cholesterol and triglyceride contents in blood were detected, and particularly, in the YMJHT 200 and 400 mg/kg and metformin co-administered groups, compared with the metformin single treated group, significant decreases (p<0.01) in total cholesterol and triglyceride contents in blood were detected (FIG. 13).

The total cholesterol content in blood changed by 219.96% in the STZ control, compared with the intact vehicle control, and changed by −30.57, −29.82, −34.29, −41.96 and −53.29% in the metformin 500 mg/kg and YMJHT 400 mg/kg single treated groups, and the YMJHT 100, 200 and 400 mg/kg and metformin 500 mg/kg co-administered groups, respectively, compared with the STZ control.

The triglyceride content in blood changed by 1986.40% in the STZ control, compared with the intact vehicle control, and changed by −29.72, −38.81, −37.65, −58.69 and −73.91% in the metformin 500 mg/kg and YMJHT 400 mg/kg single treated groups, and the YMJHT 100, 200 and 400 mg/kg and metformin 500 mg/kg co-administered groups, respectively, compared with the STZ control.

3.5.2. Change in Total LDL and HDL Contents in Blood

In the STZ control, compared with the intact vehicle control, a significant increase (p<0.01) in blood LDL content and a significant decrease in blood HDL content were detected, but in all of the administered groups, compared with the STZ control, a significant decrease (p<0.01 or p<0.05) in blood LDL content and a significant increase in blood HDL content were detected. Particularly, in the YMJHT 400 mg/kg and metformin co-administered groups, compared with the metformin single treated group, a significant decrease (p<0.01 or p<0.05) in blood LDL content and a significant increase in blood HDL content were detected, and in the YMJHT 200 mg/kg and metformin co-administered group, compared with the metformin single treated group, a significant increase (p<0.05) in blood HDL content was not detected, but a considerable decrease in blood LDL content was detected (FIG. 13).

The blood LDL content changed by 206.52% in the STZ control, compared with the intact vehicle control, and changed by −29.08, −29.79, −29.08, −39.72 and −46.10% in the metformin 500 mg/kg and YMJHT 400 mg/kg single treated groups, and the YMJHT 100, 200 and 400 mg/kg and metformin 500 mg/kg co-administered groups, respectively, compared with the STZ control.

The blood HDL content changed by −63.95% in the STZ control, compared with the intact vehicle control, and changed by 27.12, 38.42, 31.64, 61.58 and 73.45% in the metformin 500 mg/kg and YMJHT 400 mg/kg single treated groups, and the YMJHT 100, 200 and 400 mg/kg and metformin 500 mg/kg co-administered groups, respectively, compared with the STZ control.

As seen from the above results, in the STZ control, a decrease in blood HDL content was detected along with the considerable increases in blood triglyceride, total cholesterol and LDL contents, but STZ-induced hyperlipidemia was considerably suppressed through all of the metformin or YMJHT administration. Particularly, in the YMJHT 400 and 200 mg/kg co-administered groups, compared with the metformin single treated group, an increase in blood HDL content was detected, along with the significant decreases (p<0.01 or p<0.05) in blood triglyceride, total cholesterol and LDL contents. Such results are considered direct evidence of the considerable increase in the effect of metformin on diabetic hyperlipidemia through the YMJHT co-administration.

3.6. Immune Activity Effect 3.6.1. Change in Thymus Weight

In the STZ control, compared with the intact vehicle control, significant decreases (p<0.01) in absolute and relative weights of the thymus were detected, but in all of the metformin and YMJHT administered groups, compared with the STZ control, significant increases (p<0.01) in thymus weight were detected. Particularly, in the YMJHT 400 and 200 mg/kg and metformin co-administered groups, compared with the metformin single treated group, significant increases (p<0.01) in absolute and relative weights of thymus were detected (FIG. 14A).

The absolute weight of the thymus changed by −87.02% in the STZ control, compared with the intact vehicle control, and changed by 73.03, 71.99, 95.85, 204.36 and 292.53% in the metformin 500 mg/kg and YMJHT 400 mg/kg single treated groups, and the YMJHT 100, 200 and 400 mg/kg and metformin 500 mg/kg co-administered groups, respectively, compared with the STZ control.

The relative weight of the thymus changed by −74.77% in the STZ control, compared with the intact vehicle control, and changed by 50.71, 54.74, 71.34, 128.44 and 202.85% in the metformin 500 mg/kg and YMJHT 400 mg/kg single treated groups, and the YMJHT 100, 200 and 400 mg/kg and metformin 500 mg/kg co-administered groups, respectively, compared with the STZ control.

3.6.2. Change in Spleen Weight

In the STZ control, compared with the intact vehicle control, significant decreases (p<0.01) in absolute and relative weights of the spleen were detected, but in all of the metformin and YMJHT administered groups, compared with the STZ control, considerable increases in relative and absolute weights of the spleen were detected. Particularly, in the YMJHT 400 and 200 mg/kg and metformin co-administered groups, compared with the metformin single treated group, significant increases (p<0.01 or p<0.05) in absolute and relative weights of the spleen were detected (FIG. 14A).

The absolute weight of the spleen changed by −65.19% in the STZ control, compared with the intact vehicle control, and changed by 31.35, 39.59, 35.61, 77.26 and 83.89% in the metformin 500 mg/kg and YMJHT 400 mg/kg single treated groups, and the YMJHT 100, 200 and 400 mg/kg and metformin 500 mg/kg co-administered groups, respectively, compared with the STZ control.

The relative weight of the spleen changed by −31.01% in the STZ control, compared with the intact vehicle control, and changed by 12.17, 23.77, 16.43, 32.29 and 39.79% in the metformin 500 mg/kg and YMJHT 400 mg/kg single treated groups, and the YMJHT 100, 200 and 400 mg/kg and metformin 500 mg/kg co-administered groups, respectively, compared with the STZ control.

3.6.3. Histopathological Change in Thymus

Figure 15:
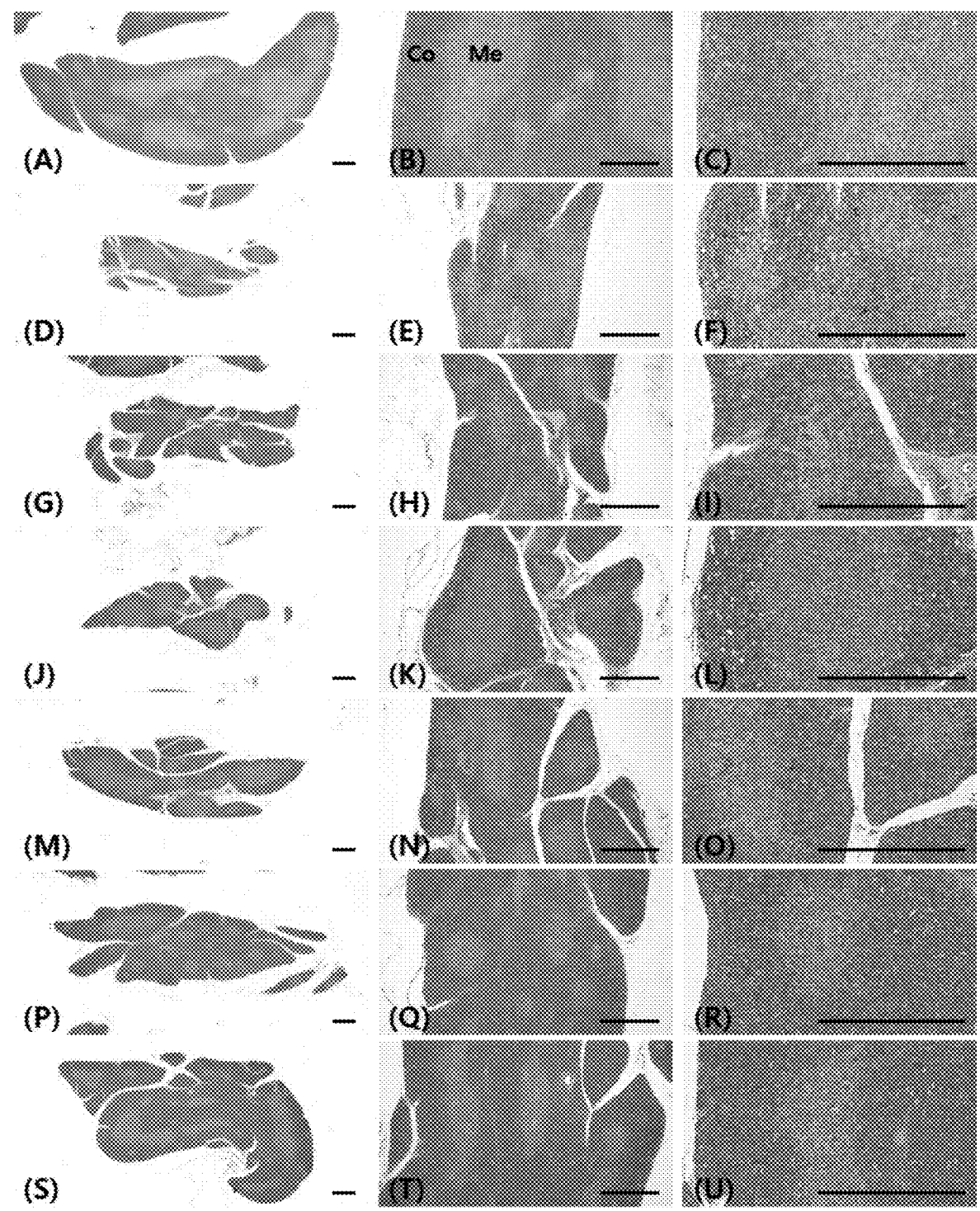
FIG. 15 shows histopathological changes in the thymus.

In the STZ control, compared with the intact vehicle control, significant decreases (p<0.01) in total thickness of the thymus cortex and lobules caused by considerable thymus contraction were detected, but in all of the metformin and YMJHT administered groups, compared with the STZ control, significant increases (p<0.01) in total thicknesses of the thymus cortex and lobules were detected. Particularly, in the YMJHT 200 and 400 mg/kg and metformin co-administered groups, compared with the metformin single treated group, significant increases (p<0.01 or p<0.05) in total thicknesses of thymus cortex and lobules were detected (FIGS. 14B and 15).

The total thickness of the thymus cortex changed by −73.92% in the STZ control, compared with the intact vehicle control, and changed by 78.00, 76.79, 91.26, 161.12 and 200.76% in the metformin 500 mg/kg and YMJHT 400 mg/kg single treated groups, and the YMJHT 100, 200 and 400 mg/kg and metformin 500 mg/kg co-administered groups, respectively, compared with the STZ control.

The total thickness of the thymus lobules changed by −86.28% in the STZ control, compared with the intact vehicle control, and changed by 198.88, 211.98, 208.55, 340.10 and 468.63% in the metformin 500 mg/kg and YMJHT 400 mg/kg single treated groups, and the YMJHT 100, 200 and 400 mg/kg and metformin 500 mg/kg co-administered groups, respectively, compared with the STZ control.

3.6.4. Histopathological Change in Spleen

Figure 16:
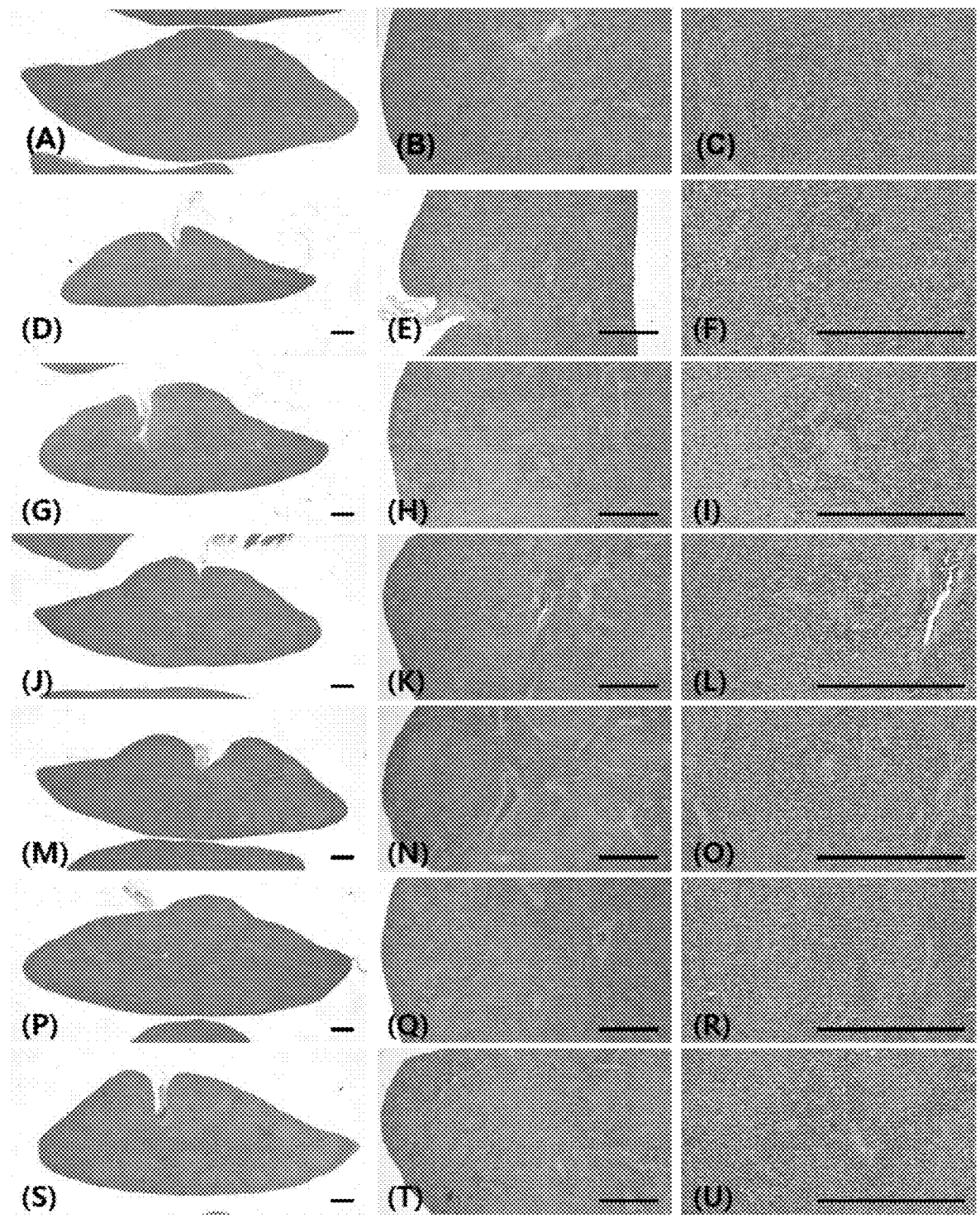
FIG. 16 shows histopathological changes in the spleen.

In the STZ control, compared with the intact vehicle control, an contraction change caused by a decrease in lymphocytes in the white pulp of the spleen was detected, and significant decreases ($p<0.01$) in spleen thickness, the number of white pulps per unit area (100 $mm^2$) and a mean diameter were detected, and in all of the administered groups, compared with the STZ control, significant increases ($p<0.01$) in spleen thickness, the number of white pulps per unit area (100 $mm^2$) and a mean diameter were detected. Particularly, in the YMJHT 200 and 400 mg/kg and metformin co-administered groups, compared with the metformin single treated group, significant increases ($p<0.01$) in spleen thickness, the number of white pulps per unit area (100 $mm^2$) and a mean diameter were detected (FIGS. 14C and 16).

The total thickness of the spleen changed by −48.50% in the STZ control, compared with the intact vehicle control, and changed by 36.43, 39.29, 36.67, 58.01 and 67.40% in the metformin 500 mg/kg and YMJHT 400 mg/kg single treated groups, and the YMJHT 100, 200 and 400 mg/kg and metformin 500 mg/kg co-administered groups, respectively, compared with the STZ control.

The number of white pulps per unit area (100 $mm^2$) changed by −71.18% in the STZ control, compared with the intact vehicle control, and changed by 76.53, 77.55, 78.57, 132.65 and 159.18% in the metformin 500 mg/kg and YMJHT 400 mg/kg single treated groups, and the YMJHT 100, 200 and 400 mg/kg and metformin 500 mg/kg co-administered groups, respectively, compared with the STZ control.

The mean diameter of the white pulp changed by −71.96% in the STZ control, compared with the intact vehicle control, and changed by 101.18, 106.90, 101.75, 179.71 and 238.87% in the metformin 500 mg/kg and YMJHT 400 mg/kg single treated groups, and the YMJHT 100, 200 and 400 mg/kg and metformin 500 mg/kg co-administered groups, respectively, compared with the STZ control.

As seen from the results, in the STZ control, histopathological contraction was detected along with the considerable decreases in thymus and spleen weights, and STZ-induced immunosuppression was considerably suppressed through all of the candidate material alone or co-administrations with 2-hour intervals. Particularly, in the YMJHT 400 and 200 mg/kg co-administered groups, compared with the metformin single treated group, a significant increase ($p<0.01$ or $p<0.05$) in immune activity effect was detected. Such results were considered direct evidence of the considerable increase in diabetic immunosuppression of metformin through the YMJHT co-administration.

3.7. Ocular Protecting Effect 3.7.1. Changes in Cataract Scores

Figure 19:
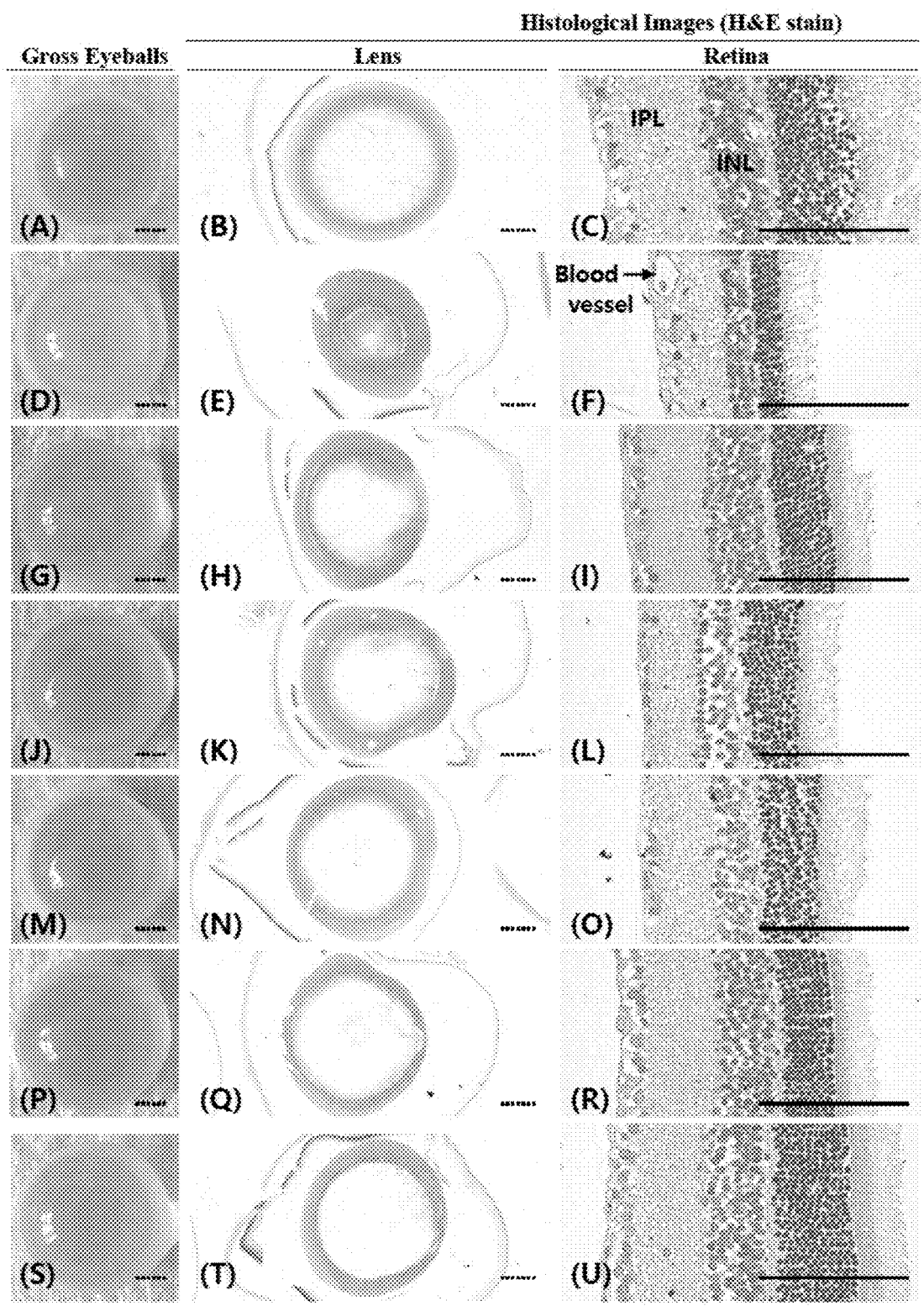
FIG. 19 shows changes in the lens and retina by group.

In the STZ control, compared with the intact vehicle control, significant increases ($p<0.01$) in observer-based and quantitative image scores for cataract were detected, but in all of the metformin and YMJHT administered groups, compared with the STZ control, significant decreases ($p<0.01$) in observer-based and quantitative image scores for cataract were detected (FIG. 17A). Particularly, in the YMJHT 200 and 400 mg/kg and metformin co-administered groups, compared with the metformin single treated group, significant decreases ($p<0.01$ or $p<0.05$) in observer-based and quantitative image scores for cataract were detected (FIGS. 18A and 19).

The observer-based scores for cataract (FIG. 17B) changed by 800.00% in the STZ control, compared with the intact vehicle control, and changed by −38.89, −30.56, −33.33, −58.33 and −66.67% in the metformin 500 mg/kg and YMJHT 400 mg/kg single treated groups, and the YMJHT 100, 200 and 400 mg/kg and metformin 500 mg/kg co-administered groups, respectively, compared with the STZ control.

The quantitative image scores for cataract changed by 553.91% in the STZ control, compared with the intact vehicle control, and changed by −40.56, −34.60, −37.61, −55.13 and −64.25% in the metformin 500 mg/kg and YMJHT 400 mg/kg single treated groups, and the YMJHT 100, 200 and 400 mg/kg and metformin 500 mg/kg co-administered groups, respectively, compared with the STZ control.

3.7.2. Histopathological Change in Lens

In the STZ control, compared with the intact vehicle control, a considerable increase in an eosinophilic degenerated part caused by non-uniform lens fibers was detected, significant increases ($p<0.01$) in the histological damage score of the lens and thickness of the degenerated part were detected, but in all of the candidate material administered groups, compared with the STZ control, significant decreases ($p<0.01$) in the histological damage score of the lens and thickness of the degenerated part were detected. Particularly, in the YMJHT 200 and 400 mg/kg and metformin co-administered groups, compared with the metformin single treated group, significant decreases ($p<0.01$ or $p<0.05$) in the histological damage score of the lens and thickness of the degenerated part were detected (FIGS. 18B and 19).

The lens damage score changed by 950.00% in the STZ control, compared with the intact vehicle control, and changed by −33.33, −38.10, −47.62, −61.90 and −71.43% in the metformin 500 mg/kg and YMJHT 400 mg/kg single treated groups, and the YMJHT 100, 200 and 400 mg/kg and metformin 500 mg/kg co-administered groups, respectively, compared with the STZ control.

The thickness of the damaged part of the lens changed by 253.66% in the STZ control, compared with the intact vehicle control, and changed by −46.34, −44.95, −51.69, −64.34 and −71.62% in the metformin 500 mg/kg and YMJHT 400 mg/kg single treated groups, and the YMJHT 100, 200 and 400 mg/kg and metformin 500 mg/kg co-administered groups, respectively, compared with the STZ control.

3.7.3. Histopathological Change in Retina

In the STZ control, compared with the intact vehicle control, significant decreases ($p<0.01$) in the total thickness of the retina caused by a considerable decrease in retina-forming cells, and thicknesses of an inner plexiform layer and an inner nuclear layer were detected, and a significant numerical increase ($p<0.01$) in blood vessels present in the retina was detected. Meanwhile, in all of the metformin and YMJHT administered groups, compared with the STZ control, significant increases ($p<0.01$) in the total thickness of the retina, and thickness of an inner plexiform layer and an inner nuclear layer, and a significant numerical decrease ($p<0.01$) in blood vessels present in the retina was detected. Particularly, in the YMJHT 200 and 400 mg/kg and metformin co-administered groups, compared with the metformin single treated group, significant increases in the total thickness of the retina, and thicknesses of an inner plexiform layer and an inner nuclear layer, and numerical decrease in blood vessels in the retina were detected ($p<0.01$ or $p<0.05$) (FIGS. 18C and 19).

The total thickness of the retina changed by −54.17% in the STZ control, compared with the intact vehicle control, and changed by 33.45, 30.69, 33.87, 56.12 and 74.15% in the metformin 500 mg/kg and YMJHT 400 mg/kg single treated groups, and the YMJHT 100, 200 and 400 mg/kg and metformin 500 mg/kg co-administered groups, respectively, compared with the STZ control.

The thickness of the plexiform layer in the retina changed by −56.07% in the STZ control, compared with the intact vehicle control, and changed by 32.03, 31.87, 34.48, 67.42 and 106.97% in the metformin 500 mg/kg and YMJHT 400 mg/kg single treated groups, and the YMJHT 100, 200 and 400 mg/kg and metformin 500 mg/kg co-administered groups, respectively, compared with the STZ control.

The thickness of the inner nuclear layer in the retina changed by −57.66% in the STZ control, compared with the intact vehicle control, and changed by 44.29, 54.06, 49.21, 77.16 and 104.14% in the metformin 500 mg/kg and YMJHT 400 mg/kg single treated groups, and the YMJHT 100, 200 and 400 mg/kg and metformin 500 mg/kg co-administered groups, respectively, compared with the STZ control.

The number of blood vessels present in an internal limiting membrane changed by 741.67% in the STZ control, compared with the intact vehicle control, and changed by −44.55, −41.58, −43.56, −59.41 and −70.30% in the metformin 500 mg/kg and YMJHT 400 mg/kg single treated groups, and the YMJHT 100, 200 and 400 mg/kg and metformin 500 mg/kg co-administered groups, respectively, compared with the STZ control.

As seen from the above results, typical diabetic ocular damage such as decreases in retina thickness, thicknesses of the inner plexiform layer and the inner nuclear layer in the retina, and proliferation of the blood vessels in the inner limiting membrane were detected in the STZ control, along with the increases in cataract and lens damage. However, through all of the metformin and YMJHT alone or co-administrations at 2-hour intervals, STZ-induced ocular damage was considerably suppressed, and particularly, in the YMJHT 400 and 200 mg/kg co-administered groups, compared with the metformin single treated group, significant increases ($p<0.01$ or $p<0.05$) in an ocular protecting effect were detected. Accordingly, the co-administration of YMJHT at 2-hour intervals was considered to considerably increase an effect of metformin on the diabetic ocular damage.

3.8. Change in Antioxidant Defense System in Kidney 3.8.1. Change in Lipid Peroxidation in Kidney In the STZ control, compared with the intact vehicle control, significant increases ($p<0.01$) in lipid peroxidation in the kidney and MDA content were detected, but in all of the metformin or YMJHT administered groups, compared with the STZ control, a significant decrease ($p<0.01$) in kidney lipid peroxidation was detected. Particularly, in the YMJHT 200 and 400 mg/kg and metformin co-administered groups, compared with the metformin single treated group, a significant decrease ($p<0.01$ or $p<0.05$) in kidney lipid peroxidation was detected (FIG. 20).

An indicator of the lipid peroxidation in the kidney tissue, a MDA content, changed by 151.18% in the STZ control, compared with the intact vehicle control, and changed by −32.56, −32.89, −36.16, −43.58 and −51.38% in the metformin 500 mg/kg and YMJHT 400 mg/kg single treated groups, and the YMJHT 100, 200 and 400 mg/kg and metformin 500 mg/kg co-administered groups, respectively, compared with the STZ control.

3.8.2. Change in Content of Renal Endogenous Antioxidant, GSH

In the STZ control, compared with the intact vehicle control, a significant decrease ($p<0.01$) in GSH content in the renal tissue was detected, but in all of the drug administered groups, compared with the STZ control, a significant increase ($p<0.01$) in GSH content was detected. Particularly, in the YMJHT 200 and 400 mg/kg and metformin co-administered groups, compared with the metformin single treated group, a significant increase ($p<0.05$) in GSH content in the renal tissue was detected (FIG. 20).

The content of the endogenous antioxidant in the renal tissue, GSH, changed by −73.41% in the STZ control, compared with the intact vehicle control, and changed by 64.65, 70.70, 68.15, 101.59 and 125.80% in the metformin 500 mg/kg and YMJHT 400 mg/kg single treated groups, and the YMJHT 100, 200 and 400 mg/kg and metformin 500 mg/kg co-administered groups, respectively, compared with the STZ control.

3.8.3. Change in Catalase and SOD Activities in Renal Tissue

In the STZ control, compared with the intact vehicle control, significant decreases ($p<0.01$) in antioxidant defense enzymes in the renal tissue, catalase and SOD activities were detected, and in all of the candidate material administered groups, compared with the STZ control, significant increases ($p<0.01$) in catalase and SOD activities were detected. Particularly, in the YMJHT 200 and 400 mg/kg and metformin co-administered groups, compared with the metformin single treated group, significant increases ($p<0.01$ or $p<0.05$) in catalase and SOD activities in the renal tissue were detected (FIG. 20).

The activity of the antioxidative defense enzyme in the renal tissue, a catalase, changed by −60.27% in the STZ control, compared with the intact vehicle control, and changed by 48.59, 47.38, 51.84, 71.36 and 91.80% in the metformin 500 mg/kg and YMJHT 400 mg/kg single treated groups, and the YMJHT 100, 200 and 400 mg/kg and metformin 500 mg/kg co-administered groups, respectively, compared with the STZ control.

The activity of an antioxidative defense enzyme in the renal tissue, SOD, changed by −55.92% in the STZ control, compared with the intact vehicle control, and changed by 51.47, 55.08, 58.96, 86.90 and 97.86% in the metformin 500 mg/kg and YMJHT 400 mg/kg single treated groups, and the YMJHT 100, 200 and 400 mg/kg and metformin 500 mg/kg co-administered groups, respectively, compared with the STZ control.

As seen from the results, an increase in MDA content and a decrease in GSH content in the renal tissues due to the lipid peroxidation were caused by the STZ administration, along with the decreases in SOD and CAT activities. Meanwhile, such an increase in MDA content and decrease in GSH content, and decreases in SOD and CAT activities were considerably suppressed by all of the metformin and YMJHT alone or co-administrations at 2-hour intervals, and particularly, in the YMJHT 400 and 200 mg/kg co-administered groups, compared with the metformin single treated group, a significant increase ($p<0.01$ or $p<0.05$) in an antioxidant effect was detected. Accordingly, the YMJHT 200 m or 400 mg/kg co-administration at 2-hour intervals was considered to considerably increase the antioxidant effect of metformin.

Accordingly, it was considered that the YMJHT 200 or 400 mg/kg co-administration at 2-hour intervals considerably increase valid effects of metformin on diabetes and diabetic liver damage, renal damage, hyperlipidemia, immunosuppression and ocular damage through activation of the antioxidant defense system. That is, it was determined that the 200 mg/kg or more YMJHT co-administration at 2-hour intervals did not influence the bioavailability of metformin, and due to the activation of the antioxidant defense system, a hypoglycemic effect of metformin was considerably increased, and various diabetic complications were reduced. Therefore, it was confirmed that the composition for treating diabetes according to the present invention, including a hypoglycemic agent and a YMJHT extract, had an excellent effect on diabetes treatment.

A composition for treating diabetes according to the present invention, which includes a YMJHT extract as an active ingredient, is co-administered with a hypoglycemic agent to improve efficiency of treating diabetes and reduce side effects occurring in the hypoglycemic agent single administration.

While the invention has been shown and described with reference to certain exemplary embodiments thereof, it will be understood by those skilled in the art that various change in form and details may be made therein without departing from the scope of the invention as defined by the appended claims. Therefore, it should be understood that the above-describe exemplary embodiments are examples in all aspects, and not limited.

We claim:

1. A method for treating type I diabetes, comprising:
    administering a composition comprising metformin and a composition comprising Yukmijihwang-tang extract to a subject in need thereof,
    wherein the Yukmijihwang-tang extract comprises *Rehmanniae Radix Preparat, Dioscoreae Rhizoma, Corni Fructus, Alismatis Rhizoma, Hoelen*, and *Moutan Cortex* with the weight ratio of 2:1:1:1:1:1.

2. The method of claim 1, wherein the composition comprising metformin and the composition comprising Yukmijihwang-tang extract are separately formulated.

3. The method of claim 1, wherein the composition comprising metformin and the composition comprising Yukmijihwang-tang extract are parenterally, orally, regionally, or percutaneously administered.

4. The method of claim 1, wherein the composition comprising Yukmijihwang-tang extract is administered within 30 minutes to 4 hours after the administration of the composition comprising metformin.

5. The method of claim 1, wherein the metformin and the composition comprising Yukmijihwang-tang extract are formulated together and are administered to the subject in a dose of from 0.001 to 300 mg/kg (body weight).

6. The method of claim 5, wherein the metformin and the composition comprising Yukmijihwang-tang extract are administered to the subject in a dose of from 0.01 to 200 mg/kg (body weight), taken together.

7. The method of claim 1, wherein the Yukmijihwang-tang extract is administered to the subject in a dose ranging from 100 mg/kg through 400 mg/kg.

8. The method of claim 1, wherein the Yukmijihwang-tang extract is administered to the subject in a dose of 100 mg/kg, 200 mg/kg or 400 mg/kg.

9. The method of claim 1, wherein the Yukmijihwang-tang extract and the metformin are administered orally.

10. The method of claim 2, wherein the Yukmijihwang-tang extract is administered before the metformin is administered.

11. The method of claim 1, wherein the metformin is administered at a dose of 500 mg/kg.

* * * * *